(12) United States Patent
Wells et al.

(10) Patent No.: US 10,487,329 B2
(45) Date of Patent: Nov. 26, 2019

(54) METHODS AND COMPOSITIONS FOR THE TREATMENT OF HEAD AND NECK CANCER

(71) Applicant: Children's Hospital Medical Center, Cincinnati, OH (US)

(72) Inventors: Susanne Wells, Cincinnati, OH (US); Allie K. Adams, Cincinnati, OH (US); Daniel Starczynowski, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/765,824

(22) PCT Filed: Oct. 26, 2016

(86) PCT No.: PCT/US2016/058864
§ 371 (c)(1),
(2) Date: Apr. 4, 2018

(87) PCT Pub. No.: WO2017/075054
PCT Pub. Date: May 4, 2017

(65) Prior Publication Data
US 2018/0282734 A1  Oct. 4, 2018

Related U.S. Application Data

(60) Provisional application No. 62/248,050, filed on Oct. 29, 2015.

(51) Int. Cl.
| | | |
|---|---|---|
| A61K 48/00 | (2006.01) | |
| C07H 21/04 | (2006.01) | |
| C12N 15/113 | (2010.01) | |
| A61K 31/4184 | (2006.01) | |
| A61K 31/5377 | (2006.01) | |
| A61K 45/06 | (2006.01) | |
| A61K 31/4375 | (2006.01) | |
| A61P 35/00 | (2006.01) | |
| A61K 31/7088 | (2006.01) | |

(52) U.S. Cl.
CPC ...... *C12N 15/1137* (2013.01); *A61K 31/4184* (2013.01); *A61K 31/4375* (2013.01); *A61K 31/5377* (2013.01); *A61K 31/7088* (2013.01); *A61K 45/06* (2013.01); *A61P 35/00* (2018.01); *C12N 2310/14* (2013.01); *C12N 2320/31* (2013.01)

(58) Field of Classification Search
CPC .............. A61K 31/713; C12N 15/111
See application file for complete search history.

(56) References Cited

U.S. PATENT DOCUMENTS

| | | | |
|---|---|---|---|
| 9,168,257 B2 | 10/2015 | Starczynowski et al. | |
| 2007/0087392 A1 | 4/2007 | Somers et al. | |
| 2013/0280264 A1 | 10/2013 | Davila | |
| 2014/0350070 A1* | 11/2014 | Starczynowski | A61K 31/5377 |
| | | | 514/44 A |

FOREIGN PATENT DOCUMENTS

| | | |
|---|---|---|
| WO | 2007047907 A2 | 4/2007 |
| WO | WO 2017/075054 A1 | 5/2017 |

OTHER PUBLICATIONS

Adams et al. (Oncotarget, vol. 6, No. 41, 2015, pp. 43395-43407).*
Adams, A.K., et al., "DEK promotes HPV-positive and -negative head and neck cancer cell proliferation," Oncogene, 2015, 34:868-877, 10 pgs.
Adams, A.K., et al., "IRAK1 is a novel DEK transcriptional target and is essential for head and neck cancer cell survival," Oncotarget, Oct. 2015, 6:43395-43407, 13 pgs.
Alexiadis, V., et al., "The protein encoded by the proto-oncogene DEK changes the topology of chromatin and reduces the efficiency of DNA replication in a chromatin-specific manner," Genes Dev, 2000, 14(11):1308-1312, 5 pgs.
Ang, K.K., et al., "Human Papillomavirus and Survival of Patients with Oropharyngeal Cancer," N Engl J Med, Jul. 2010, 363(1):24-35, 21 pgs.
Campillos, M., et al., "Transcriptional activation by AP-2α is modulated by the oncogene DEK," Nucleic Acids Res, 2003, 31(5):1571-1575, 5 pgs.
Cerami, E., et al., "The cBio Cancer Genomics Portal: An Open Platform for Exploring Multidimensional Cancer Genomics Data," Cancer Discovery, May 2012, 2(5):401-404, 5 pgs.
Chaturvedi, A.K., et al., "Human Papillomavirus and Rising Oropharyngeal Cancer Incidence in the United States," J Clin Oncol, Nov. 2011, 29(32):4294-4301, 8 pgs.
Chen, J., et al., "ToppGene Suite for gene list enrichment analysis and candidate gene prioritization," Nucleic Acids Res, 2009, 37(Web Server issue):W305-W311, 7 pgs.
Datta, A., et al., "Oncoprotein DEK as a tissue and urinary biomarker for bladder cancer," BMC Cancer, 2011, 11:234, 7 pgs.
Edgar, R., et al., "Gene Expression Omnibus. NCBI gene expression and hybridization array data repository," Nucleic Acids Res, 2002, 30(1):207-210, 4 pgs.
Fang, J., et al., "Cytotoxic effects of bortezomib in myelodysplastic syndrome/acute myeloid leukemia depend on autophagy-mediated lysosomal degradation of TRAF6 and repression of PSMA1," Blood, 2012, 120(4):858-867, 10 pgs.

(Continued)

*Primary Examiner* — Amy H Bowman
(74) *Attorney, Agent, or Firm* — Davis Wright Tremaine LLP

(57) ABSTRACT

Disclosed are methods of treating a head and/or neck squamous cell carcinoma in an individual. The method may include the step of administering to an individual a composition comprising an interleukin-1 receptor-associated kinase 1 (IRAK1) inhibitor, which may include inhibitors that inhibit IL-1 receptor-associated kinase 1 in addition to other IL-1 receptor-associated kinases, such as, for example, an IRAK1/4 inhibitor.

11 Claims, 20 Drawing Sheets

(56) References Cited

OTHER PUBLICATIONS

Flicek, P., et al., "Ensembl 2012," Nucleic Acids Res, 2012, 40(Database issue):D84-90, 7 pgs.
Gao J, et al., "Integrative Analysis of Complex Cancer Genomics and Clinical Profiles Using the cBioPortal," Science Signaling, Apr. 2013, 6(269):1-19, 19 pgs.
Hung, P-S., et al., "miR-146a Enhances the Oncogenicity of Oral Carcinoma by Concomitant Targeting of the IRAKI, TRAF6 and NUMB Genes," PloS One, 2013, 8(11):e79926, 17 pgs.
Kavanaugh, G.M., et al., "The human DEK oncogene regulates DNA damage response signaling and repair," Nucleic Acids Res, 2011, 39(17):7465-7476, 12 pgs.
Khodadoust, M.S., et al., "Melanoma Proliferation and Chemoresistance Controlled by the DEK Oncogene," Cancer Res, Aug. 2009, 69(16):6405-6413, 9 pgs.
Ko, S-I., et al, "Regulation of histone acetyltransferase activity of p300 and PCAF by proto-oncogene protein DEK," FEBS Leters, 2006, 580(13):3217-3222, 6 pgs.
Koch, A.T., et al., "MyD88-Dependent Signaling Decreases the Antitumor Efficacy of Epidermal Growth Factor Receptor Inhibition in Head and Neck Cancer Cells," Cancer Res, 2015, 75(8):1657-1667, 11 pgs.
Koleva, R.I., et al., "C/EBPα and DEK coordinately regulate myeloid differentiation," Blood, 2012, 119(21):4878-4888, 39 pgs.
Komurov, K., et al., "NetWalker: a contextual network analysis tool for functional genomics," BMC Genomics, 2012, 13:282, 9 pgs.
Marur, MD, S., et al., "Head and Neck Cancer: Changing Epidemiology, Diagnosis, and Treatment," Mayo Clinic Proceedings, 2008, 83(4):489-501, 13 pgs.
Mor-Vaknin, N., et al., "DEK in the Synovium of Patients With Juvenile Idiopathic Arthritis: Characterization of DEK Antibodies and Posttranslational Modification of the DEK Autoantigen," Arthritis and Rheumatism, Feb. 2011, 63(2):556-567, 12 pgs.
Mor-Faknin, N., et al., "The DEK Nuclear Autoantigen Is a Secreted Chemotactic Factor," Mol Cell Biol, 2006, 26(24):9484-9496, 13 pgs.
Privette Vinnedge, L.M., et al., "The DEK Oncogene Is a Target of Steroid Hormone Receptor Signaling in Breast Cancer," PloS One, 2012, 7(10):e46985, 10 pgs.
Privette Vinnedge, L.M., et al., "The DEK oncogene promotes cellular proliferation through paracrine Wnt signaling in Ron receptor-positive breast cancers," Oncogene, 2015, 34:2325-2336, 12 pgs.
Privette Vinnedge, L.M., et al, "The human DEK oncogene stimulates α-catenin signaling, invasion and mammosphere formation in breast cancer," Oncogene, 2011, 30(24):2741-2752, 12 pgs.

Remington: The Science and Practice of Pharmacym 21$^{st}$ Edition, 2005, Troy, D.B., ed., Lippincott Williams & Wilkins publishing, Philadelphia, 6 pgs. Table of Contents only.
Remington's Pharmaceutical Sciences, 18$^{th}$ Edition, 1990, Gennaro, A.R. ed., Mack Publishing Company, Easton, Pennsylvania, 8 pgs. Table of Contents only.
Rhyasen, G.W., et al., "IRAK signalling in cancer," British Journal of Cancer, 2015, 112:232-237, 6 pgs.
Rhyasen, G.W., et al., "Targeting IRAK1 as a Therapeutic Approach for Myelodysplastic Syndrome," Cancer Cell, Jul. 2013, 24(1):90-104, 15 pgs.
Sammons, M., et al., "Negative Regulation of the RelA/p65 Transactivation Function by the Product of the DEK Proto-oncogene," J Biol Chem, 2006, 281(37):2682-26812, 11 pgs.
Sandén, C., et al., "The DEK oncoprotein binds to highly and ubiquitously expressed genes with a dual role in their transcriptional regulation," Molecular Cancer, 2014, 13:215, 13 pgs.
Sawatsubashi, S., et al., "A histone chaperone, DEK, transcriptionally coactivates a nuclear receptor," Genes Dev, 2010, 24(2):159-170, 13 pgs.
Shibata, T., et al., "DEK oncoprotein regulates transcriptional modifiers and sustains tumor initiation activity in high-grade neuroendocrine carcinoma of the lung," Oncogene, 2010, 29(33):4671-4681, 11 pgs.
Srivastava, R., et al., "Augmentation of therapeutic responses in melanoma by inhibition of IRAK-1,-4," Cancer Res, 2012, 72(23):6209-6216, 29 pgs.
Starczynowski, D.T., et al., "Identification of miR-145 and MiR-146a as mediators of the 5q- syndrome phenotype," Nat Med, Jan. 2010, 16(1):49-58, 11 pgs.
Wise-Draper, T.M., et al., "Apoptosis Inhibition by the Human DEK Oncoprotein Involves Interference with p53 Functions," Mol Cell Biol, Oct. 2006, 26(20):756-7519, 14 pgs.
Xie, X., et al., "Systematic discovery of regulatory motifs in human promoters and 3' UTRs by comparison of several mammals," Nature, Mar. 2005, 434(7031):338-345, 19 pgs.
International Search Report and Written Opinion dated Jan. 19, 2017 for Application No. PCT/US2016/058864, 11 pgs.
U.S. Appl. No. 62/248,050, filed Oct. 29, 2015.
U.S. Appl. No. 16/339,692, filed Apr. 4, 2019.
U.S. Appl. No. 14/284,521, filed May 22, 2014.
U.S. Appl. No. 14/842,049, filed Sep. 1, 2015.
U.S. Appl. No. 15/288,402, filed Oct. 7, 2016.
U.S. Appl. No. 16/326,571, filed Feb. 19, 2019.

* cited by examiner

FIG 1A
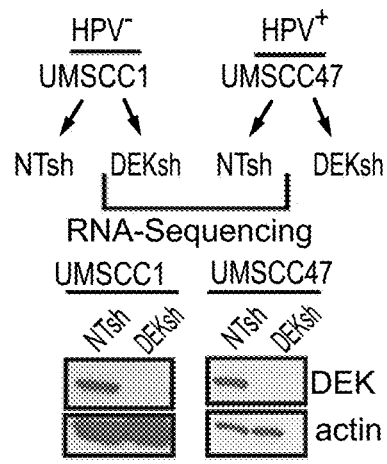
FIG 1B
Overview DEKsh/NTsh FC≥1.4
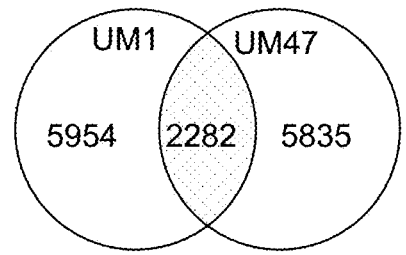
Up-regulated DEKsh/NTsh FC≥1.4
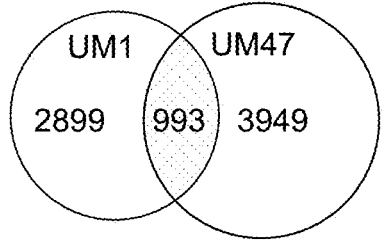
Down-regulated DEKsh/NTsh FC≥1.4
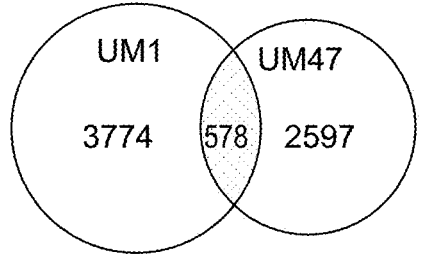

FIG 1C

| Biological Process: | p-value |
|---|---|
| Biological Adhesion | $6.29 \times 10^{-13}$ |
| Cell Adhesion | $8.65 \times 10^{-13}$ |
| Positive Regulation of Developmental Processes | $5.89 \times 10^{-9}$ |
| Positive Regulation of Cell Differentiation | $8.01 \times 10^{-9}$ |
| Positive Regulation of Immune System Process | $8.68 \times 10^{-9}$ |
| Regulation of Multicellular Organismal Development | $2.15 \times 10^{-8}$ |
| Blood Vessel Development | $3.02 \times 10^{-8}$ |
| Positive Regulation of Response to Stimulus | $4.48 \times 10^{-8}$ |
| Vasculature Development | $7.26 \times 10^{-8}$ |
| Regulation of Immune System Process | $1.02 \times 10^{-7}$ |

FIG 1D

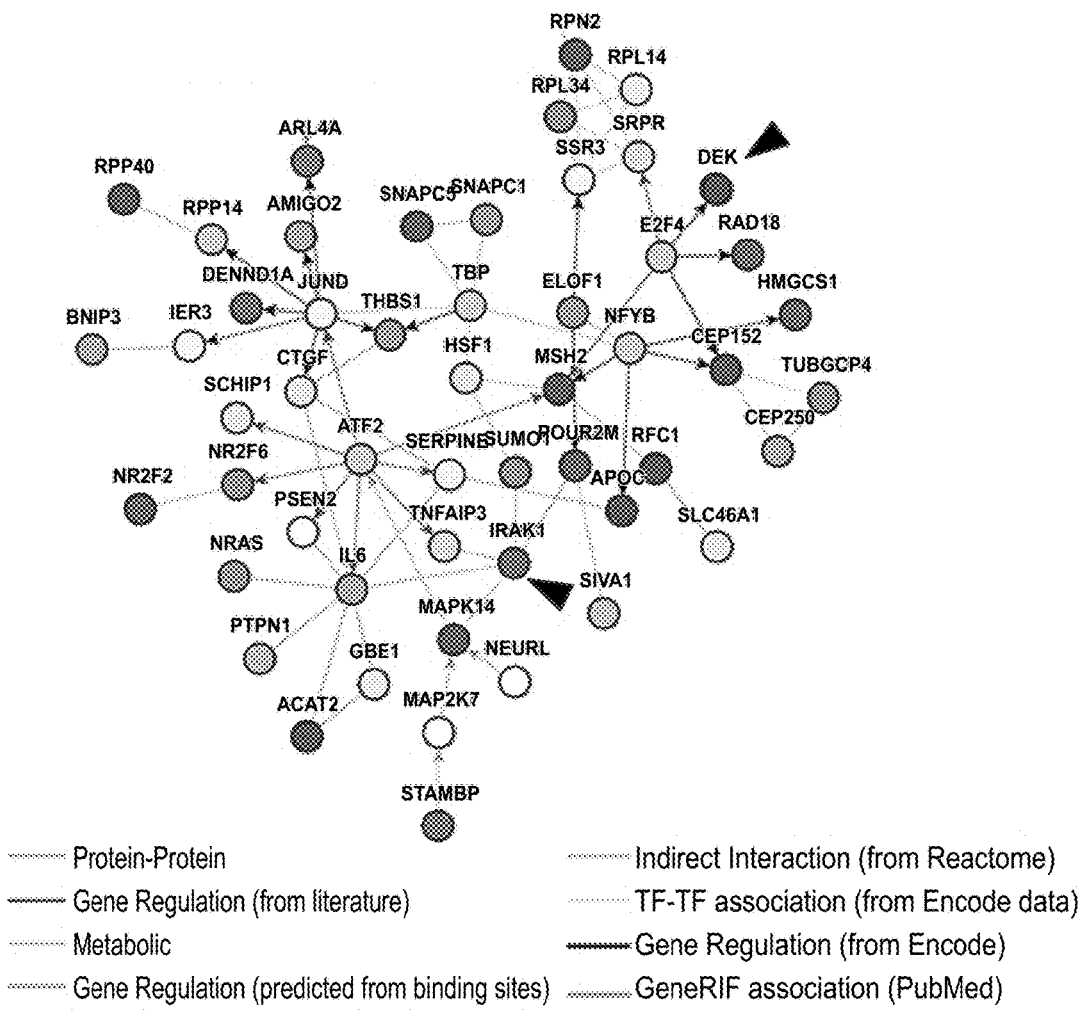

FIG 2A
Fold Change (DEKsh/NTsh):
| | UMSCC1 | UMSCC47 |
|---|---|---|
| DEK | -57.65 | -9.76 |
| IRAK1 | -3.22 | -1.43 |
FIG 2B
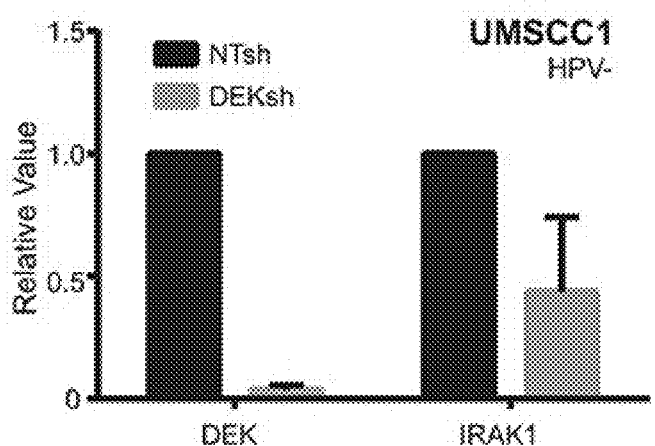
FIG 2C
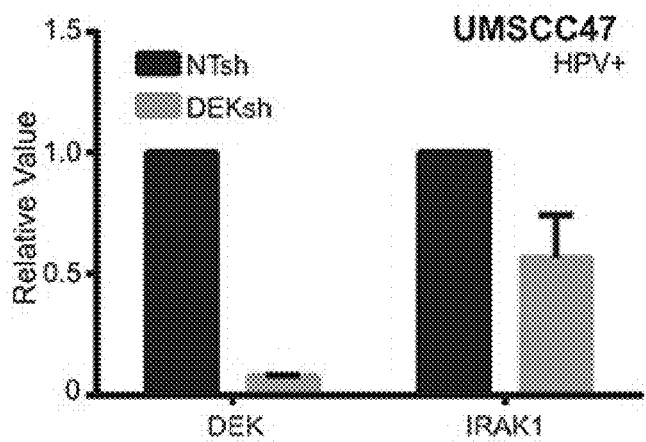

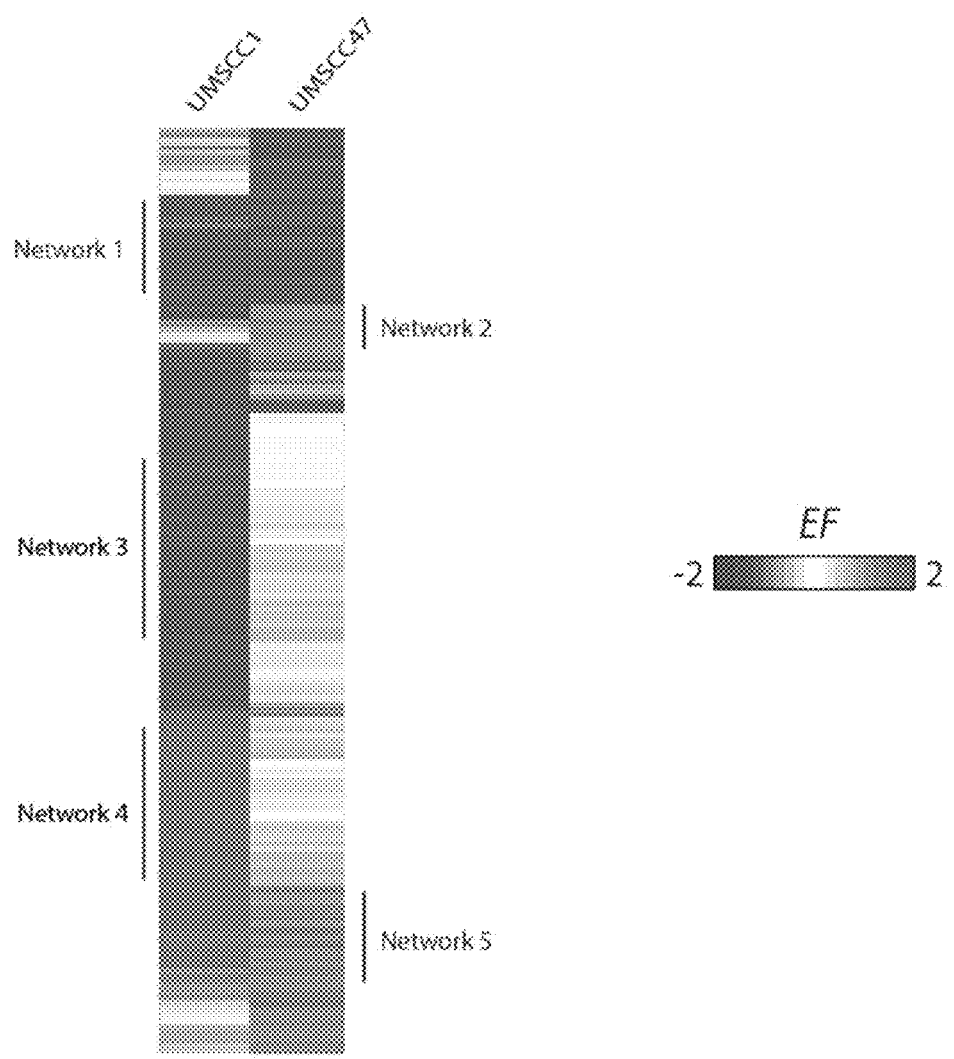

FIG. 12
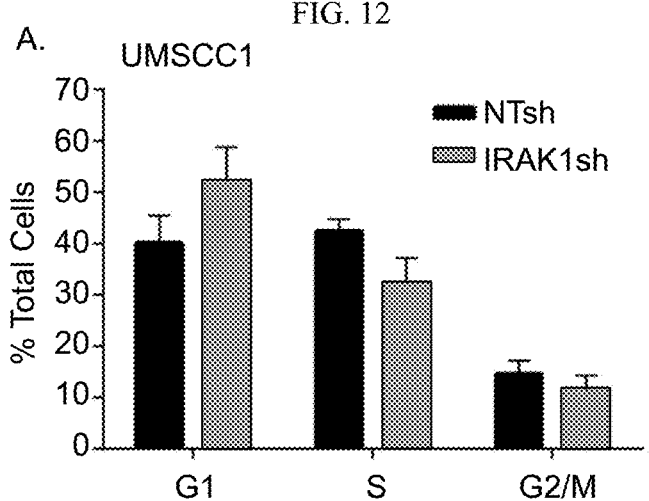
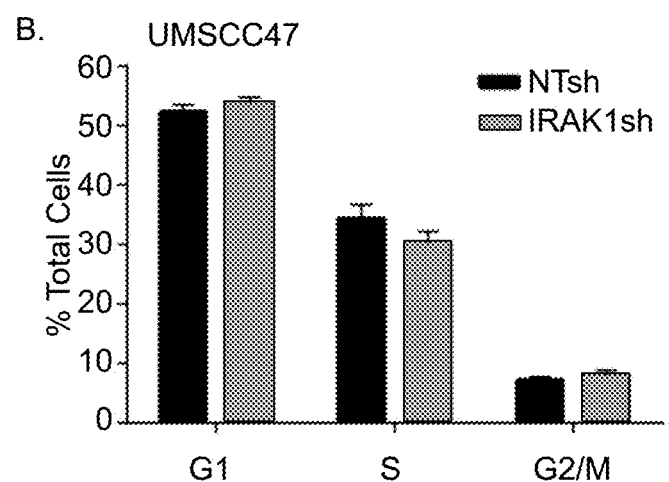
FIG 13 (supp fig 8).
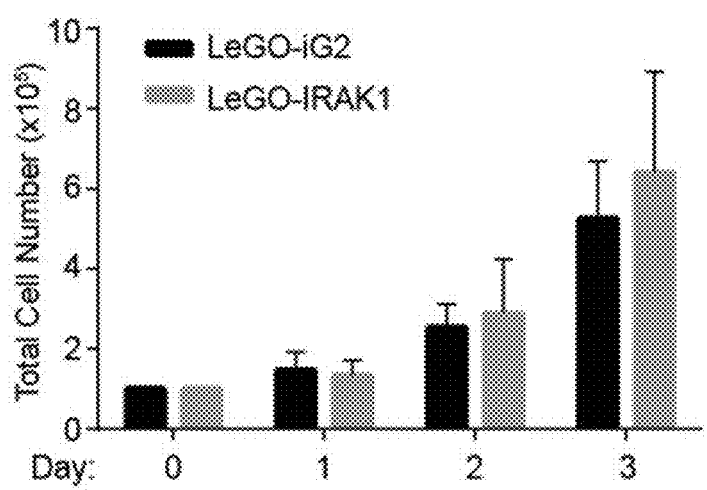

METHODS AND COMPOSITIONS FOR THE TREATMENT OF HEAD AND NECK CANCER

CROSS REFERENCE TO RELATED APPLICATIONS

This application claims priority to and benefit of International Application No. PCT/US2016/058864, entitled "Methods and Compositions for the Treatment of Head and Neck Cancer," filed Oct. 26, 2016, which claims priority to and benefit of U.S. Provisional Application Ser. No. 62/248,050 filed Oct. 29, 2015 entitled "Methods and Compositions for the Treatment of Head and Neck Cancer," the contents of which are incorporated herein it its in their entirety for all purposes.

STATEMENT REGARDING FEDERALLY SPONSORED RESEARCH OR DEVELOPMENT

This invention was made with government support under CA116316 awarded by the National Institutes of Health. The government has certain rights in the invention.

BACKGROUND

Head and neck squamous cell carcinoma (HNSCC) is a disease comprised of two distinct entities: human papillomavirus (HPV) positive and HPV negative. HPV− disease is attributable to tobacco and alcohol use, and its declining incidence in the US has been ascribed to the well-publicized health risks of these activities. In stark contrast, HPV+ disease is on the rise, particularly in younger patient populations [1]. While improved response to traditional chemotherapies and thus favorable long-term survival is observed in HPV+ patients, prognoses remain grim for patients with advanced and metastatic tumors [2]. Furthermore, major quality of life issues arise due to treatment-related tissue damage [3]. Therefore, there is a need in the art for novel therapeutic targets and biomarkers for both HNSCC subsets. The instant disclosure seeks to address one or more of these needs in the art.

BRIEF SUMMARY

Disclosed are methods of treating a head and/or neck squamous cell carcinoma in an individual. The method may include the step of administering to an individual a composition comprising an interleukin-1 receptor-associated kinase 1 (IRAK1) inhibitor, which may include inhibitors that inhibit IL-1 receptor-associated kinase 1 in addition to other IL-1 receptor-associated kinases, such as, for example, an IRAK1/4 inhibitor.

BRIEF DESCRIPTION OF THE DRAWINGS

FIG. 1A-FIG. 1D. Profiling the DEK-dependent transcriptome in HNSCC. (FIG. 1A) UMSCC1 and UMSCC47 were lentivirally depleted for DEK, as confirmed by western blot analysis, and mRNA from these lines was submitted for RNA-Sequencing (RNA-Seq). (FIG. 1B) GeneSpring NGS analysis was performed on genes differentially expressed 1.4 fold or greater (DEKsh/NTsh). GeneSpring derived Venn diagrams depict genes altered in both cell lines and overlap highlights genes common to both UMSCC1 and UMSCC47. (FIG. 1C) Overlapping genes (from panel B, 2282) from UMSCC1 and UMSCC47 were analyzed using ToppGene server to identify significantly altered biological processes. The top 10 biological processes are represented. (FIG. 1D) A portion of the down-regulated gene networks analyzed on NetWalker highlights nodes containing IRAK1 and DEK in UMSCC1 cells. A full view of view of this map can be found in FIG. 7.

FIG. 2A-FIG. 2E. DEK regulates IRAK1 mRNA and protein levels. (FIG. 2A) Table depicts fold changes for DEK and IRAK1 in UMSCC1 and UMSCC47 from GeneSpring NGS analysis. (FIG. 2B, FIG. 2C, FIG. 2D) IRAK1 mRNA is reduced following DEK depletion. IRAK1 and DEK mRNA levels were confirmed by TaqMan qRT-PCR to validate RNA-Seq results in three cell lines: UMSCC1, UMSCC47, and UMSCC6 (HPV negative). Experiments were performed twice and standard deviation (SD) depicted. (FIG. 2E) Western blot analysis confirms IRAK1 protein levels and downstream signaling are also depleted in the absence of DEK. Actin was used as a loading control.

(FIG. 3A) cBioPortal analysis of the TOGA HNSCC database reveals IRAK1 alterations occur in 14% of HNSCC. A total of 279 samples were analyzed and were further broken down into HPV− and HPV+ subsets. (FIG. 3B) IRAK1 is expressed in primary HNSCC tissues. CCHMC-HNSCC1 (HPV+) and CCHMC-HNSC18 (HPV−) were stained for IRAK1 by immunohistochemistry, with intense staining in both the nucleus and cytoplasm. n=4 samples were stained. Images were taken at 5× and 20× magnification. (FIG. 3C) IRAK1 staining is not expressed in well differentiated layers of normal human skin (NHSK) from unrelated donors. Images were taken at 20× magnification.

(FIG. 4A) IRAK1 loss attenuates activation of downstream signaling pathways in HNSCC. UMSCC1 and UMSCC47 were transduced with control (NTsh) or IRAK1 knockdown (IRAK1sh) vectors and protein was collected following selection in puromycin. Whole cell lysates were analyzed by western blot analysis to confirm IRAK1 knockdown, along with reduction in IRAK1 activation (pIRAK1Thr209) and MAPK pathways. GAPDH was used as a loading control. (FIG. 4B) IRAK1-inhibitor reduces IRAK1 activation in HPV+ and HPV− cell lines. UMSCC1 and UMSCC47 cells were plated and DMSO (control) or IRAK1-inhibitor was added the following day at 1 μM or 10 μM final concentrations. Cells were then collected for western blot analysis at indicated time-points. Inhibition of IRAK1 was confirmed by western blot analysis, as measured by phosphorylation of IRAK1. GAPDH was used as a loading control. (FIG. 4C, FIG. 4 D) TRAF6 ubiquitination is reduced following IRAK1 loss. Immunoprecipitation was performed on RIPA lysates with the TRAF6 antibody. Western blot was then performed for ubiquitin. Remaining whole cell lysates were analyzed by western blot for TRAF6, IRAK1, and GAPDH. (FIG. 4E, FIG. 4 F) IRAK1 loss increases cellular death via apoptosis. Cells were analyzed by flow cytometry for cleaved-caspase 3 conjugated to FITC. Experiments were performed in triplicate with SEM depicted. (FIG. 4G) IRAK1-inhibitor increases apoptosis. UMSCC1 cells were plated and DMSO or IRAK1-inhibitor was added after cells attached. Cells and media were collected 72 hours later and analyzed for cleaved caspase-3 by flow cytometry. Experiment was performed three times, with SEM depicted. (*=p<0.05).

(FIG. 5A) IRAK1 overexpression rescues ERK1/2 signaling. Sorted control or IRAK1 overexpressing cells were transduced with control (NTsh) or DEK knockdown (DEKsh) vector. After selection was complete protein was collected and analyzed by western blot. GAPDH was used as a loading control. Growth curves of control (iG2) versus IRAK1 overexpressing cells can be found in FIG. 13. (FIG. 5B) IRAK1 and DEK regulate cell growth and viability independently. Cells from (FIG. 5A) were used to analyze apoptosis (FIG. 5B), cellular cycle (FIG. 5C), and cellular proliferation. (FIG. 5D) IRAK1 overexpression did not rescue the phenotypes observed with DEK loss. Experiments were performed twice and SD is represented. (FIG. 5E) Combined IRAK1 and DEK loss increases cell death. Control and IRAK1 knockdown cells were transduced with control (AdGFP) or DEK knockdown (AdDEKsh) adenovirus. Three days post-adenoviral infection cells were collected and later analyzed for cleaved caspase-3 by flow cytometry. Graph represents fold change compared to NTsh AdGFP samples. Experiments were performed twice and SD represented. (FIG. 5F) Molecular model.

FIG. 6. Network analysis was performed with Netwalker software on UMSCC1 and UMSCC47 RNA-Seq data. Labeled Networks 1-5 can be seen in expanded views in FIGS. 7-11.

FIG. 12. UMSCC1 and UMSCC47 cells with IRAK1 knockdown reveals no alterations in cell cycle profiles. PrdU incorporation was measured by flow cytometry to determine G1, S, and G2/M populations. Experiments were performed in triplicate.

FIG. 13. UMSCC1 IRAK1 overexpression cells (IRAK1) do not exhibit cell growth difference over controls (iG2). Cells were plated at equal densities and counted over three days. Experiments were performed in duplicate.

DETAILED DESCRIPTION OF THE INVENTION

Definitions

Figure 2D:
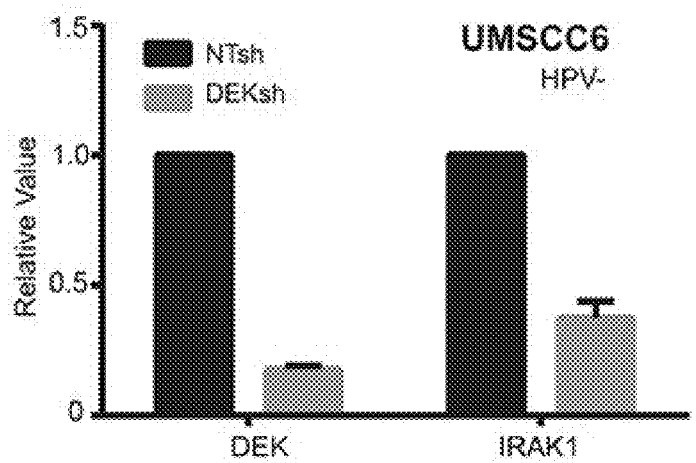

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms refer to children.

"Therapeutically effective amount" relates to the amount or dose of an active compound or composition described herein that will lead to one or more therapeutic effect, in particular desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase "pharmaceutically acceptable," as used in connection with compositions of the disclosure, refers to molecular entities and other ingredients of such compositions that are physiologically tolerable and do not typically produce untoward reactions when administered to a subject (e.g., human). In certain embodiments, as used herein, the term "pharmaceutically acceptable" means approved by a regulatory agency of a Federal or a state government or listed in the U.S. Pharmacopeia or other generally recognized pharmacopeia for use in mammals (e.g., humans).

The term "carrier" applied to pharmaceutical compositions of the disclosure refers to a diluent, excipient, or vehicle with which an active compound (e.g., dextromethorphan) is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" by E. W. Martin, 18th Edition.

The term "compound," as used herein, is also intended to include any salts, solvates, or hydrates thereof.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of dextromethorphan and/or quinidine can also be suitable for use in the compositions and methods disclosed herein. In certain embodiments, the dextromethorphan is administered in the form of dextromethorphan hydrobromide, and the quinidine is administered in the form of quinidine sulfate. A salt of a compound of this disclosure may be formed between an acid and a basic group of the compound, such as an amino functional group, or a base and an acidic group of the compound, such as a carboxyl functional group. According to another embodiment, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In one aspect, a method of treating head and/or neck squamous cell carcinoma in an individual is disclosed. The method may comprise the steps of administering to said individual a composition comprising an interleukin-1 receptor-associated kinase 1 (IRAK1) inhibitor, which may include inhibitors that inhibit IL-1 receptor-associated kinase 1 in addition to other IL-1 receptor-associated kinases, such as, for example, an IRAK1/4 inhibitor.

In one aspect, the head and/or neck squamous cell carcinoma may be characterized by DEK overexpression. In one aspect, the head and/or neck squamous cell carcinoma may be characterized by IRAK1 overexpression in a cell or tissue of said head and/or neck squamous cell carcinoma. In one aspect, the head and/or neck squamous cell carcinoma may be human papillomavirus (PV) positive. In one aspect, the head and/or neck squamous cell carcinoma may be human papillomavirus (PV) negative.

In one aspect, the IRAK1 and/or an IRAK1/4 inhibitor may be selected from N-acyl-2-aminobenzimidazoles, imidazo[1,2-a]pyridino-pyrimidine, imidazo[1,2-a]pyridino-pyridine, benzimidazolo-pyridine, N-(2-morpholinylethyl)-2-(3-nitrobenzoylamido)-benzimidazole, (available from Sigma Aldrich, 15409 SIGMA), LG0224912 (TG Therapeutics), LG0250276 (TG Therapeutics), an IRAK inhibitor as described in US 20150284405 A1, or combinations thereof.

In one aspect, the IRAK1 and/or an IRAK1/4 inhibitor may comprise an RNAi sufficient to inhibit IRAK1 expression.

In one aspect, the administering step may be selected from orally, rectally, nasally, topically, parenterally, subcutaneously, intramuscularly, intravenously, transdermally, or a combination thereof.

In one aspect, the administration may decrease the growth or metastasis of said head and/or neck squamous cell carcinoma in said individual, as compared to an individual not receiving said composition.

In one aspect, the method may decrease a marker of viability of head and/or neck squamous cell carcinoma cells.

In one aspect, the treatment may decrease a marker of viability of head and/or neck squamous cell carcinoma, wherein marker is selected from survival over time, proliferation, growth, migration, formation of colonies, chromatic assembly, DNA binding, RNA metabolism, cell migration, cell adhesion, inflammation, or a combination thereof.

In one aspect, composition may further comprise an inhibitor of DEK.

In one aspect, a method of diagnosing and treating a head and/or neck squamous cell carcinoma in an individual is disclosed, in which the method may comprise the steps of
 a) obtaining a plasma sample from the individual;
 b) detecting a IRAK1 protein or gene expression level in the sample;
 c) diagnosing the individual with a head and/or neck squamous cell carcinoma when the IRAK1 protein or gene expression level is increased in said sample as compared to a protein or gene expression level of IRAK1 in a healthy control; and
 d) administering an effective amount of an IRAK1 inhibitor to the individual.

In one aspect, the administration step may further comprises administering a DEK inhibitor.

Dosage

As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual patient response.

In certain embodiment, the dosage of the composition provided herein, based on weight of the active compound, administered to prevent, treat, manage, or ameliorate a disorder, or one or more symptoms thereof in a subject may be about 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In one aspect, the active ingredient or a pharmaceutically acceptable salt thereof, may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a condition can be readily determined by an ordinarily skilled physician The pharmaceutical compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The dosage of the one or more of the disclosed active agents or a pharmaceutically acceptable salt thereof used to achieve a therapeutic effect will depend not only on such factors as the age, weight and sex of the patient and mode of administration, but also on the degree of inhibition desired and the potency of the one or more of the disclosed active agents or a pharmaceutically acceptable salt thereof for the particular disorder or disease concerned. It is also contemplated that the treatment and dosage of the one or more of the disclosed active agents or a pharmaceutically acceptable salt thereof may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

Routes of Administration

Any suitable route of administration can be employed for providing the patient with an effective dosage of the disclosed compositions. For example, oral, rectal, transdermal, parenteral (subcutaneous, intramuscular, intravenous), intrathecal, topical, inhalable, and like forms of administration can be employed. Suitable dosage forms include tablets, troches, dispersions, suspensions, solutions, capsules, patches, and the like. Administration of medicaments prepared from the compounds described herein can be by any suitable method capable of introducing the compounds into the bloodstream. In some embodiments, the formulations can contain a mixture of active compounds with pharmaceutically acceptable carriers or diluents known to those of skill in the art.

The compositions can be prepared in any desired form, for example, tables, powders, capsules, injectables, suspensions, sachets, cachets, patches, solutions, elixirs, and aerosols. Carriers such as starches, sugars, microcrystalline cellulose, diluents, granulating agents, lubricants, binders, disintegrating agents, and the like can be used in oral solid preparations. In certain embodiments, the compositions are prepared as oral solid preparations (such as powders, capsules, and tablets). In certain embodiments, the compositions are prepared as oral liquid preparations. In some embodiments, the oral solid preparations are tablets. If desired, tablets can be coated by standard aqueous or non-aqueous techniques.

In addition to the dosage forms set out above, the compounds disclosed herein can also be administered by sustained release, delayed release, or controlled release compositions and/or delivery devices.

Pharmaceutical compositions suitable for oral administration can be provided as discrete units such as capsules, cachets, sachets, patches, injectables, tablets, and aerosol sprays, each containing predetermined amounts of the active ingredients, as powder or granules, or as a solution or a suspension in an aqueous liquid, a non-aqueous liquid, an oil-in-water emulsion, or a water-in-oil liquid emulsion. Such compositions can be prepared by any of the conventional methods of pharmacy, but the majority of the methods typically include the step of bringing into association the active ingredients with a carrier which constitutes one or more ingredients. In general, the compositions are prepared by uniformly and intimately admixing the active ingredients with liquid carriers, finely divided solid carriers, or both, and then, optionally, shaping the product into the desired presentation.

For example, a tablet can be prepared by compression or molding, optionally, with one or more additional ingredients. Compressed tablets can be prepared by compressing in a suitable machine the active ingredient in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

A composition or formulation may be administered to a subject continuously or periodically.

The compositions or fractions thereof may comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. Suitable pharmaceutical diluents, excipients, vehicles, and carriers are described in the standard text, Remington: The Science and Practice of Pharmacy (21st Edition. 2005, University of the Sciences in Philadelphia (Editor), Mack Publishing Company. By way of example, for oral administration in the form of a capsule or tablet, the active components can be combined with an oral, non-toxic pharmaceutically acceptable inert carrier such as lactose, starch, sucrose, methyl cellulose, magnesium stearate, glucose, calcium, sulfate, dicalcium phosphate, mannitol, sorbital, and the like. For oral administration in a liquid form, the agents may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof.

In one aspect, a pharmaceutical composition may have pH from about 7 to about 10.

Formulations for parenteral administration of a composition may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. methylhydroxybenzoate or similar additives.

In an embodiment, a solid form pharmaceutical composition is provided (e.g. tablets, capsules, powdered, or pulverized form) comprising one or more of the disclosed active agents or salt thereof.

In another embodiment, a liquid drug formulation is provided and comprises a pharmaceutically acceptable salt of one or more of the disclosed active agents or salt thereof, and to lyophilized drug formulations that can be reconstituted to provide suspensions that are stable and suitable for parenteral administration.

A composition described herein may be sterilized by, for example, filtration through a bacteria retaining filter, addition of sterilizing agents to the composition, irradiation of the composition, or heating the composition. Alternatively, the compounds and compositions may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition, such labeling would include amount, frequency, and method of administration.

Kits

In one aspect, kits are disclosed. A kit may comprise, for example, a composition comprising an agent selected from an IRAK1, and IRAK1/4 inhibitor, an inhibitor of DEK, and a combination thereof and a pharmaceutically acceptable carrier; and a means for delivery of the composition to a human.

Further disclosed is an article of manufacture comprising a container comprising a label; and a composition comprising an agent selected from an IRAK1, and IRAK1/4 inhibitor, an inhibitor of DEK, and a combination thereof, wherein the label indicates that the composition is to be administered to an individual having, suspected of having, or at risk for developing, a head and/or neck squamous cell carcinoma.

In one aspect, a kit comprises or consists essentially of agents or compositions described herein. The kit may be a package that houses a container which may contain a composition as disclosed herein, and also houses instructions for administering the agent or composition to a subject. In one aspect, a pharmaceutical pack or kit may be provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, the invention encompasses kits in which components of the compositions are packaged separately. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In an aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that may be diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of one or more of the disclosed active agents, or a pharmaceutically acceptable salt thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

EXAMPLES

DEK is important in various cancer cell types, including breast and bladder cancer, melanoma, and most recently, HNSCCs [4-8]. This is a versatile nuclear protein, with functions that range from chromatin modifier and histone chaperone to modulator of DNA repair, replication, and transcription [9-12]. For example, DEK represses transcription in leukemia cells through inhibition of p300 and P/CAF [13]. DEK also activates transcription via interaction with AP-2a in glioblastoma [14]. Although DEK has been published as a co-activator or co-repressor of transcription in various systems, transcriptome data to determine the role of DEK in global transcriptional regulation in solid tumors is scarce [14-16].

Applicant's previous work highlighted the oncogenic functions of DEK in both HPV+ and HPV− human HNSCCs, wherein DEK was highly overexpressed and required for optimal growth and proliferation [8]. Dek loss of function in mice attenuated the proliferation of HPV16 E7 expressing, but not normal, epidermis and inhibited overt tumor growth in a chemically induced model of HNSCC. Furthermore, this work implicated ΔNp63 as a downstream DEK target that regulated DEK-dependent proliferation. In view of the observed specificity of DEK targeting for pre- and overt malignancies, this molecule has been reported as a potential therapeutic target. However, DEK-dependent signaling pathways and molecular mediators of DEK-dependent tumor phenotypes in HNSCC are limited. Herein, Applicant aimed to uncover relevant pathways important in DEK-dependent HNSCC phenotypes that may also be novel therapeutic strategies.

In this study, Applicant performed transcriptome profiling to identify DEK-dependent gene regulatory networks essential for HNSCC. Applicant focused on both subsets of HNSCC, HPV− and HPV+, to identify targets that may be beneficial to patients regardless of HPV status. Following gene ontological analysis, biological processes involved in the immune response were strongly implicated. DEK has previously been published as an autoantigen in autoimmune diseases and it can function as a pro-inflammatory protein, suggesting it may regulate inflammatory signaling [17, 18]. Central to the immune response pathway and a significantly repressed target following DEK knockdown is IRAK1, a serine/threonine kinase, which mediates signaling from the toll-like receptor (TLR) and interleukin-1 receptors (IL1R) [19]. The IRAK1 signaling cascade includes the E3 ubiquitin ligase TRAF6, which engages, among other pathways, NF-κB and MAPK signaling. IRAK1 was recently implicated as a novel therapeutic target in myelodysplastic syndrome (MDS) and acute myeloid leukemia (AML), but its function in most solid tumors remains unknown [20]. Applicant found that IRAK1 is overexpressed by genomic amplification and transcriptional up-regulation in a significant proportion of HNSCC tumors. Furthermore, genetic or pharmacologic inhibition of IRAK1 attenuated downstream signaling through TRAF6 and increased apoptosis, suggesting IRAK1 inhibition may be a new therapeutic target in HNSCC. Finally, DEK and IRAK1 contributed to HNSCC survival independently, and targeting them jointly enhanced HNSCC cell death over the targeting of either. Taken together, these data reveal IRAK1 as a component of the DEK transcriptome, and a druggable effector in HNSCC.

Results

Figure 10:
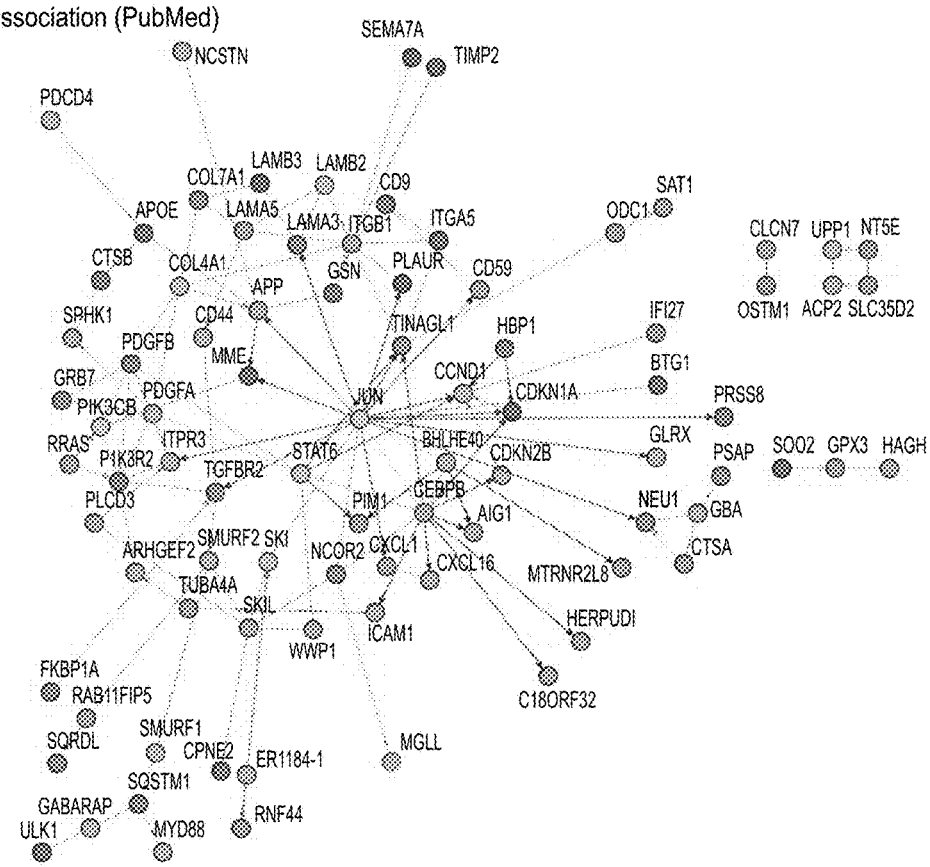
FIG. 10. Network 4 is represented, with genes up-regulated in UMSCC1, with log fold change represented.
Figure 11:
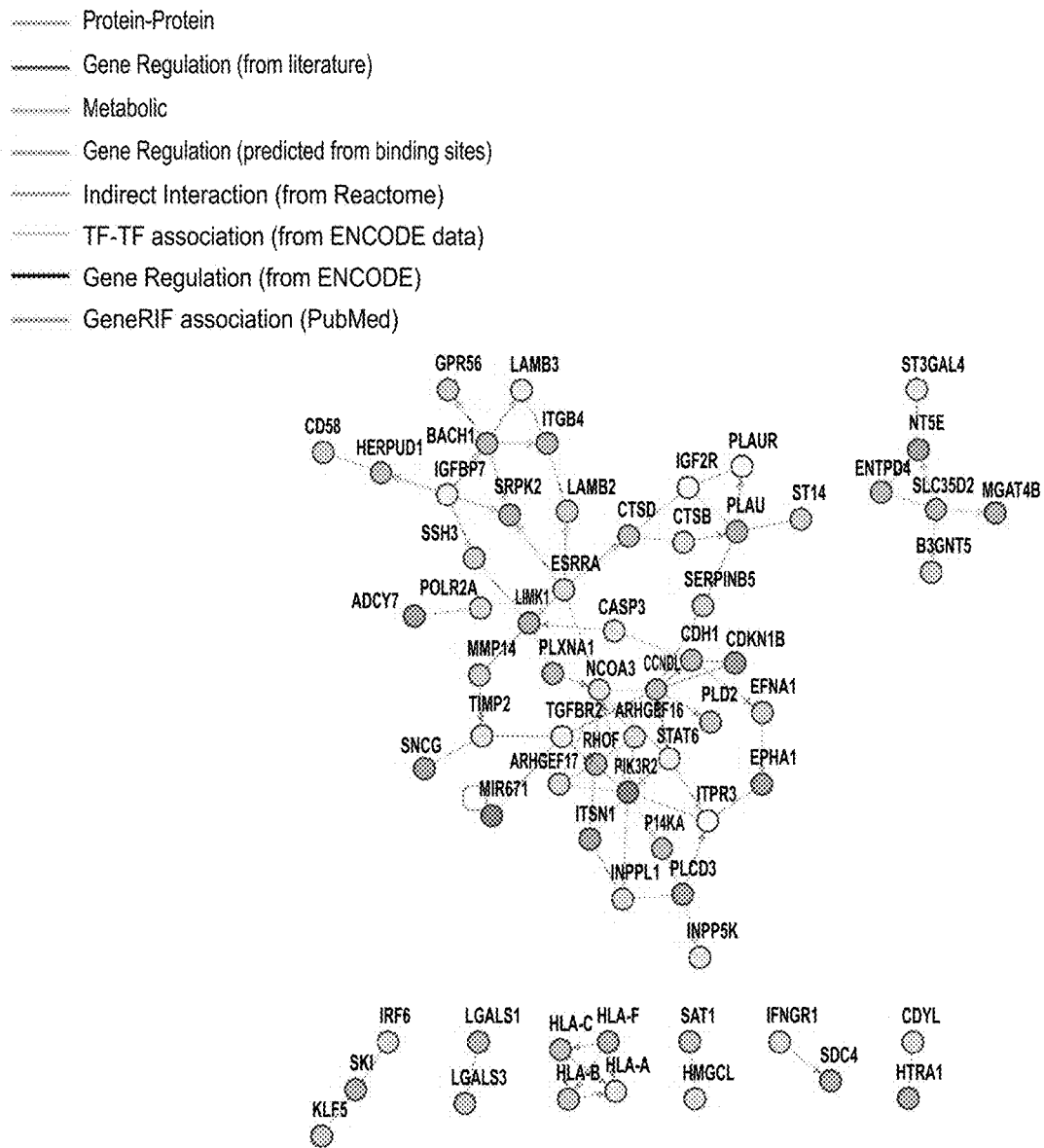
FIG. 11. Network 5 is represented, with genes up-regulated in UMSCC1, with log fold change represented.

Profiling the DEK-dependent transcriptome in HNSCC. Little is known about the global impact of DEK loss on gene expression, and relevant transcriptional targets are largely uncharacterized [16]. DEK plays dual roles in transcription, either as a co-activator or a co-repressor depending on the cellular context, and was recently published to bind transcriptional start sites of some of the activated or repressed target genes [12]. In order to define the consequences of DEK loss and identify DEK-dependent transcriptional networks in HNSCC cells, Applicant used a well-established lentiviral approach that was previously published in this model system [8]. The HPV− and HPV− cell lines, UMSCC1 and UMSCC47, respectively, were transduced with DEK versus control knockdown vector and selected with puromycin. Successful knockdown was confirmed by western blot analysis (FIG. 1A). Messenger RNA (mRNA) was collected and subjected to RNA-Seq. Independent analyses were 131 performed on UMSCC1 and UMSCC47 RNA-Seq data to identify fold changes for differentially expressed genes. Venn diagrams highlight over 2,000 common genes that were differentially expressed upon DEK loss in these cell lines (FIG. 1B). Ontology analyses revealed dysregulation of the immune response pathway (FIG. 10).

Specifically, immune response genes were down-regulated in DEK-deficient cells. In parallel, Applicant assessed common transcription factor binding sites among the overlapping gene set, and identified many new sites, along with published ones such as p53 consensus sequences (Tables 1-3) [21].

TABLE 1

Transcription factor binding site (TFBS) analysis for genes up-regulated in UMSCC1 and UMSCC47.

| TF binding site ID | log p-value | Up-regulated Genes |
|---|---|---|
| V$P53_DECAMER_Q2 | 2.972 | ABCA12, AKAP6, ARHGEF37, ARHGEF6, BCL11B, DOCK9, FLRT1, GJB4, HCAR2, HOXB3, KRT15, LRP1, PIM1, PITPNC1, PPL, PRDM12, PTAFR, PTPRG, RAP2B, RARB, ST5, TBC1D8, TECTA |
| V$E12_Q6 | 2.61 | ABLIM3, ALDH1A2, ARVCF, CAMK2A, COL4A3, CORO2B, CPZ, CRELD1, GFAP, GJB2, HIF3A, ITGB4, MDGA1, MYH14, NFATC4, NPEPPS, POU2F3, SASH1, SELL, SORCS2, SPTB |
| RTAAACA_V$FREAC2_01 | 2.452 | ABCA1, ABLIM3, ACVR1C, ADAMTS13, ARHGEF6, ARID4A, ASAH1, BACH2, BCL11B, BIK, C1QTNF3, CCND1, CDKN1B, DAPP1, DOCK3, EMP1, EPHB3, FBXW7, GATS, GCNT2, GPR110, GPR4, GRK5, HCAR2, HCAR3, HOXA5, HSPG2, IL16, L3MBTL1, LEMD1, LRP1, MAML3, MGAT4B, MMP13, MN1, NEBL, NGEF, NLGN3, NR4A2, PBXIP1, PCDHGA5, PHEX, PIK3IP1, PITPNC1, PLAG1, PLAU, PPAP2B, PRDM1, PROX1, RP1, RPS6KA5, SDCBP2, SLC34A3, SLC4A1, SOCS1, SPRY4, TCF7L2 |
| V$TAL1BETAE47_01 | 2.11 | ABHD16A, ASB4, DTX2, HOXB6, HRK, KCNIP2, NPR2, OMG, PBXIP1, PCDH1, PCDH12, PHEX, PLXNA3, PPAP2B, PYY, RCAN2, RNF19A, SCN1B, UPK2, WNT9A |
| V$1RF_Q6 | 1.932 | ACSL5, ARHGEF6, CCND1, DAPP1, ESR1, HLA-C, HLA-F, HOXB3, MLLT3, MUSK, NCF1, NPEPPS, PLXNC1, PSMB10, SELL, SOCS1, TCF7L2, ZBP1 |
| V$AREB6_01 | 1.876 | CDKN1B, CEL, CRELD1, CSAD, CYP26B1, FBXO24, FXYD3, GAD1, HOXB6, IQGAP2, MAP3K5, PCDHGA5, PLAG1, PROX1, RRAD, S100A9, SLC4A11, STRC, STX1A, VWF |
| KRCTCNNNNMANAGC_UNKNOWN | 1.816 | HIST1H1C, HIST1H2AC, HIST1H2AJ, HIST1H2BD, HIST1H2BJ, HIST2H2AC, HIST2H2BE, HIST3H2BB |
| V$P53_02 | 1.809 | ABCA12, ACSL5, AKAP6, ASIC4, BCL11B, FLRT1, GAD1, GCNT2, HCAR2, KRT15, NR4A3, PIK3R2, PITPNC1, PPL, PRDM12, PTPRG, RARB, ST5, TMC7 |
| TGANNYRGCA_V$TCF11MAFG_01 | 1.77 | ABCC6, ANGPTL4, ATL1, BCL6, CBX6, CLCN5, CPZ, DRP2, DTX2, ESR1, FBLN2, LRP1, NR4A3, OMG, PFKFB1, |

TABLE 1-continued

Transcription factor binding site (TFBS) analysis for genes up-regulated in UMSCC1 and UMSCC47.

| TF binding site ID | log p-value | Up-regulated Genes |
|---|---|---|
| TGTTTGY_V$HNF3_Q6 | 1.76 | PIM1, PRDM1, RAG1, SLC22A18, TFEC, TREML2 ALDH1A2, ARHGEF6, ASB4, BCL11B, BCL6, CBX6, CDH12, CNTNAP2, CSAD, DOCK9, DTX2, EFNA1, ESR1, FCGBP, FLRT1, GJB4, HCAR1, HCAR2, HCAR3, HIST1HIC, HIST1H2BD, HOXB3, HS3ST5, IL16, IQGAP2, ITM2B, MAST4, MGAT4B, MUSK, NFATC4, NOS3, NR4A3, OMG, PDGFRA, PHEX, PRDM1, PTPRG, SHC3, SLC4A11, SNCG, SPAG8, ST5, TCF7L2, TFEC |
| V$AML1_01 | 1.701 | ACSL5, AKAP3, ANXA8L2, CD6, EMP1, GRK5, MMP13, MMP14, MPL, MR1, PDZK1, PLXNCI, RAG1, S100A9, SCEL, SLC37A2, STRC, TLL2 |
| V$AML1_Q6 | 1.701 | ACSL5, AKAP3, ANXA8L2, CD6, EMP1, GRK5, MMP13, MMP14, MPL, MR1, PDZK1, PLXNCI, RAG1, S100A9, SCEL, SLC37A2, STRC, TLL2 |
| YATGNWAAT_V$OCT_C | 1.68 | ACBD4, ALDH1A2, ARHGAP4, CCND1, DNAH5, EPHB3, FBXO24, GPR4, HIST1H2AC, HIST2H2AC, HIST2H2BE, HOXA5, HOXB6, MMP17, NR4A3, PFKFB1, PIWIL4, POU2F3, PRDM1, RARB, RNASE4, SASH1, SEMA6C, SH3BGRL, WNT9A |
| V$PPARA_02 | 1.644 | AHCYL2, CBX6, CDH17, EPHB1, HOXA5, MNT, NLGN3, PSCA, RTN2, SERPINF2, UCN2 |
| V$PPARA_01 | 1.64 | CD36, PAPLN, PDZK1, PTPRG, ZNF547 |
| V$FREAC4_01 | 1.603 | ADAMTS13, ALDH1A2, EMP1, HSPG2, MAST4, PHEX, PRDM1, PTAFR, SLC34A3, SPRY4, TCF7L2, TECTA |
| RYCACNNRNNRNCAG_UNKNOWN | 1.543 | AHCYL2, FYB, IL17RE, MB, PBXIP1, RHOF, UPK2 |
| V$NFKAPPAB65_01 | 1.48 | COL11A2, CSF1R, CYP2D6, DSC2, GNG4, GRK5, KCNN2, KRT23, PCDH12, POU2F3, PRDM12, PTGES, SDC4, TCEA2, TRIB2, TSLP, ZMYND15 |
| V$GATA_Q6 | 1.475 | ABCA12, COL4A3, DENND1B, EPB42, FMO1, GPR116, HOXB6, HS3ST5, PDGFRA, PFKFB1, PLAG1, PVRL4, SLC4A1, SPRY4, SYT7 |
| TGCCAAR_V$NF1_Q6 | 1.47 | ABCA9, ABLIM2, AGER, AQP11, ARHGEF6, BACH2, BCL6, C1QTNF3, C4A, C4B, C6orf223, CLCN5, COL4A3, DDO, EIF4EBP3, ESR1, FLRT1, GCNT2, GFAP, GNAT2, IL16, INHBC, MAST4, MPL, MUSK, NAPB, NLGN3, PAPLN, PAQR6, PBXIP1, PHEX, PLXNC1, PROX1, RARB, RPS6KA5, RRAD, SPRY4, SYTL2, TSLP, VNN2, XDH |
| V$PAX4_03 | 1.442 | AGER, ANXA4, CBX6, COL11A2, FBXO24, HIF3A, HOXB6, KCNN2, LRP1, MMP14, MNT, MPL, NFATC4, NLGN3, PPAP2B, PRDM1, SERPINI1, TRIM46 |

TABLE 1-continued

Transcription factor binding site (TFBS) analysis for genes up-regulated in UMSCC1 and UMSCC47.

| TF binding site ID | log p-value | Up-regulated Genes |
| --- | --- | --- |
| RTTTNNNYTGGM_UNKNOWN | 1.39 | ALDH1A2, ESR1, FHIT, LRP1, MARCO, MAST4, NOS3, PHEX, PTPRCAP, PTPRG, STX6, TECTA |
| TGACATY_UNKNOWN | 1.376 | ACVR1C, AKAP3, AOC2, ARHGAP4, ARHGEF6, ASB11, ASB4, CLCN5, DSC2, FAM71F1, FBXO32, HOXB3, ITM2B, KCNN2, LEMD1, LRP1, MLLT3, MNT, NEBL, NFATC4, PBXIP1, PDGFRA, PITPNC1, PLAG1, PRDM1, PTPRC, RAPSN, RARB, RCAN2, RNF19A, RRAD, SASH1, SH3BGR, SLC4A1, ST5, STX6, TBC1D8, TECTA |
| V$CEBP_01 | 1.358 | BCL11B, CLDN16, CSAD, CYP2D6, DOCK9, EVI2A, GCNT2, GSTA4, HOXB3, HOXB6, MNT, NFATC4, PFKFB1, PLXNC1, PRDM1, RNF19A, S100A9, ST5 |
| V$OCT_C | 1.358 | ARHGAP4, EPHB3, FBXO24, GCNT2, GPR4, HIST1H2AC, HIST2H2AC, HIST3H2BB, HOXB3, MMP17, PFKFB1, POU2F3, PRDM1, SASH1, SEMA6C, SH3BGRL, STAT4, TLL2 |
| GATAAGR_V$GATA_C | 1.336 | ABCA12, ADPRHL1, EPB42, FCGBP, FMO1, HS3ST5, HYAL3, KRT15, KRT23, LEMD1, MLLT3, MST1, NEBL, PFKFB1, PLAG1, PTPRC, SLC34A3, SLC4A1, SPRY4, SYT7 |
| V$COREBINDINGFACTOR_Q6 | 1.326 | ADD1, ANXA8L2, B3GNT5, CD6, CYGB, EMP1, EVI2A, HOXB6, IL17RE, MMP13, MPL, NR4A3, PDZK1, PITPNC1, RAG1, S100A9, SLC37A2, STRC |
| CCANNAGRKGGC_UNKNOWN | 1.323 | ACBD4, GAD1, GRK5, LRP1, MB, PCDH12, POU2F3, SORCS2, UPK2 |
| V$HNF4_Q6 | 1.307 | ABCA12, ARHGEF37, C4A, C4B, EMP1, FBXW7, HOXA5, PDZK1, PRDM1, PROX1, PTPRH, RARB, SLC5A2, SLPI, SP140, SPINT1, SULT2B1 |

Enriched TFBS were found using the ToppGene server

TABLE 2

Transcription factor binding site analysis for genes down-regulated in UMSCC1 and UMSCC47.

| TFbindingsiteID | log p-value | Down-regulated Genes |
| --- | --- | --- |
| V$SRF_C | 3.17 | ACVR1, CYR61, DIXDC1, EMILIN2, HOXA3, MAPK14, MYL9, NR2F2, PPP2R3A, RAB30, SCOC, TAGLN, THBS1, TNNC1, ZAK |
| V$SRF_Q4 | 2.907 | DIXDC1, EDN1, EMILIN2, HOXA3, MAPK14, MYL9, NR2F2, PPP2R3A, RAB30, SCOC, TAGLN, THBS1, TNNC1, VGF, ZAK |
| CTTTAAR_UNKNOWN | 2.802 | ANKRD28, ATP5SL, AXL, CREB3L1, CYR61, DCX, DOCK11, EDN1, EGLN3, ETHE1, FPGT, GAN, GNG11, GNGT1, HOXA3, HOXA4, HPS3, KCTD8, KIRREL3, KTN1, MAPKAPK3, NELL2, NR2F2, NR5A2, PDE3B, PLXDC2, PPM1E, PPP2R3A, PXK, RBM24, SCD, |

TABLE 2-continued

Transcription factor binding site analysis for genes down-regulated in UMSCCI and UMSCC47.

| TFbindingsiteID | log p-value | Down-regulated Genes |
|---|---|---|
| | | SCML1, SMARCA1, SOCS2, STEAP2, TAGLN, TBX2, TCF4, TGFB2, VGF, ZNF593 |
| TGGAAA_V$NFAT_Q4_01 | 2.689 | ANKRD28, ANTXR1, APOM, ARHGEF25, CALB1, CCNI, CD86, CDC42EP3, CKS1B, CNIH1, COL2A1, CXCL10, CYR61, DNMT3B, EFNB3, ERBB4, FAM155B, FZD7, GDA, GFOD1, GPR150, HOXA13, HOXA3, HOXA4, HSPH1, HTR7, IL6, IL7R, KCNQ5, KIRREL3, LRRC2, MGP, MTX2, NGF, NINJ2, NR5A2, NRAS, PAK1IP1, PDE3B, PIGW, POLG2, PPP2CA, PPP2R3A, RAB30, RCN3, RNF128, SCRN3, SKP2, SLA, SLC43A1, SMYD2, SNX12, SOCS2, STEAP2, SV2A, TBX2, TCF12, TCF4, TGFB2, TJP2, TNFRSF11B, TUB, VEGFC, VGF, XPNPEP1, ZIC5, ZNF593 |
| CCAWWNAAGG_V$SRF_Q4 | 2.622 | DIXDC1, RAB30, SCOC, TAGLN, TCF4, THBS1, TNNC1, ZAK |
| V$COUP_01 | 2.506 | APOM, CKS1B, CNIH1, DOCK11, EFNB3, FAM155B, HOXA3, IL21R, NR2F2, NYAP1, PDE3B, PPP2R3A, RPL34, SMYD5, STEAP2 |
| V$ER_Q6_02 | 2.506 | ADAMTS15, CAPN12, CD37, DACT2, DCX, FHL1, HOXA3, HPCAL4, KIRREL3, MTX2, NR2F6, PPM1E, SMARCA1, STEAP2, TOMM40 |
| V$EN1_01 | 2.073 | ERBB4, FHL1, HOXA4, HTR7, MAPK14, NRAS, PEX2, TCF4 |
| V$MYC_Q2 | 2.068 | CA14, COL2A1, HPCAL4, LDHA, NRAS, PFDN2, SC5D, SHMT2, SLC43A1, TGFB2, ZNF593 |
| V$NMYC_01 | 1.978 | ANGPT2, BCL2, CA14, COL2A1, GJA1, MAPKAPK3, NRAS, RAB30, RNF128, SC5D, SLC43A1, SOCS5, VGF, ZCCHC7 |
| V$OCT1_01 | 1.978 | CDC42EP3, CYR61, EGLN3, HOXA3, HPCAL4, IRAK1, LHX6, NR2F2, PPP2R3A, PYGO1, SLC19A3, SLC7A11, TCF12, TCF4 |
| RYTGCNNRGNAAC_V$MIF1_01 | 1.826 | BTG4, EFNB3, HMGCS1, HSF1, LHX6, ZNF593 |
| V$SMAD_Q6 | 1.813 | BCL2, CCNI, CKS1B, GARNL3, KCNQ5, LHX6, NYAP1, PRX, SMARCA1, SMYD2, SNX12, SYT11, TAGLN |
| V$NFAT_Q4_01 | 1.69 | ANKRD28, HOXA3, KCNQ5, KIRREL3, MRPL30, NR5A2, PAK1IP1, PDE3B, PPP2R3A, RNF128, SCRN3, SLA, TJP2 |
| V$NRF2_01 | 1.68 | BCL2, C11orf84, CKS1B, E2F4, FBXO22, HSPH1, NRAS, PAFAH1B2, RPL34, TIMM8B, TOMM40, ZNF22 |
| CACGTG_V$MYC_Q2 | 1.618 | ANGPT2, BEX2, CA14, COL2A1, DZIP1, GAR1, GJA1, HOXA3, HOXA4, HPCAL4, HPS3, HSPH1, KCNQ5, KIAA1033, LDHA, MAPKAPK3, NPTX1, NRAS, PDP2, PDPR, PFDN2, PIGW, RAB30, RNF128, RRS1, SC5D, SHMT2, SLC43A1, SOCS2, SOCS5, TBC1D5, TCF4, TGFB2, VGF, ZCCHC7, ZNF593 |
| V$MYCMAX_02 | 1.603 | ANGPT2, APLN, COL2A1, DZIP1, HOXA3, HSPH1, KCNQ5, LRRC2, RAB30, RNF128, TCF4, TGFB2, VGF |
| AAGWWRNYGGC_UNKNOWN | 1.583 | ANKRD28, HOXC10, IRAK1, NRAS, PPM1E, RFC1, SMYD5 |
| TAAWWATAG_V$RSRFC4_Q2 | 1.577 | BEX2, GRB14, HOXA4, KCNQ5, KTN1, PPP2R3A, SV2A, TCF4, TNNC1 |
| V$CEBP_Q3 | 1.516 | CYR61, DYRK3, EFNA5, GPLD1, NR2F2, PPM1E, RAB30, SNX12, TCF12, TGFB2, WNT10B, ZAK |
| V$RSRFC4_Q2 | 1.501 | ADAM11, BNIP3, CDC42EP3, KCNQ5, KTN1, MRPS23, PTPN1, SCML1, SLCO2A1, SV2A, TNNC1 |
| V$POU3F2_02 | 1.46 | BBX, CYR61, DIXDC1, HOXA3, HOXA4, HPCAL4, IRAK1, LHX6, NRAS, OLFML2B, PAK1IP1, PDE3B |
| V$STAT5A_03 | 1.46 | BBX, GPR150, HOXA3, HOXA4, HOXC10, MAPK14, PDE3B, PLXDC2, PPP2R3A, SV2A, TCF4, TNFRSF11B |
| V$MEF2_Q6_01 | 1.46 | ADAM11, ANGPT2, CDC42EP3, GAN, GRB14, KCNQ5, KTN1, LRRC2, PRX, SMARCA1, SV2A, TNNC1 |

TABLE 2-continued

Transcription factor binding site analysis for genes down-regulated in UMSCCI and UMSCC47.

| TFbindingsiteID | log p-value | Down-regulated Genes |
|---|---|---|
| V$ELK1_02 | 1.457 | CKS1B, DDIAS, FBXO22, MTX2, NRAS, OGG1, RFC4, TIMM8B, TOMM40, TRO, ZNF22 |
| WWTAAGGC_UNKNOWN | 1.456 | BBX, DCX, ETHE1, IRAK1, MYL9, NR2F2, NRAS, TBX2 |
| V$CEBP_Q2 | 1.442 | EDN2, LHX6, MAPK14, NR2F2, PDE3B, PTX3, PYGO1, RRM2B, SKP2, TCF12, TCF4 |
| GAANYNYGACNY_UNKNOWN | 1.43 | CKS1B, GDA, NR2F2, SUMO1, TCF12 |
| V$FOXD3_01 | 1.428 | ANKRD28, CYR61, DIXDC1, HOXA3, KCNQ5, NRAS, PRICKLE2, RNF128, SLC39A8, TGFB2 |
| V$SRF_Q6 | 1.42 | DIXDC1, EMILIN2, HOXA3, LDHA, MYL9, NR2F2, PPP2R3A, SCOC, TAGLN, THBS1, TNNC1, ZAK |
| V$OCT1_05 | 1.394 | BCL2, EDN1, HOXA3, IL6, LHX6, NR2E1, PPM1E, PPP2R3A, SCML1, SLC19A3, SLC7A11, TCF12 |
| V$USF_Q6_01 | 1.372 | APLN, HOXA3, KIAA1033, NPTX1, NRAS, PDP2, PFDN2, SC5D, SLC43A1, SOCS5, VGF |
| V$ATF1_Q6 | 1.372 | CCNI, CD37, DOK1, DYRK3, HOXA4, HOXC10, KCTD8, LDHA, NR2E1, RRM2B, VGF |
| V$CP2_02 | 1.358 | CDC42EP3, DCX, DDIT4, FOXL2, RAB30, RNF121, TBC1D5, TBX2, TNNC1, WNT10B, XPNPEP1 |
| V$USF_02 | 1.342 | APLN, CA14, CYR61, FAM155B, NPTX1, NYAP1, PFDN2, RFC1, RNF128, TCF12, TGFB2, UBE2L6 |
| V$SRF_Q5_01 | 1.331 | DIXDC1, EMILIN2, MAPK14, MYL9, NR2F2, NRAS, PPP2R3A, SCOC, TAGLN, THBS1, ZAK |
| V$IK1_01 | 1.317 | CD86, IL6, LHX6, MMP16, NEK4, NR2F6, RNF128, SMYD2, SOCS2, TNFSF18, VGF, ZIC5 |

Enriched TFBS were found using ToppGene server

TABLE 3

Transcription factor binding site analysis for genes differentially expressed in both UMSCC1 and UMSCC47, but oppositely regulated (up vs. down).

| TF binding site ID | log p-value | Oppositely-Regulated Genes |
|---|---|---|
| V$GATA6_01 | 1.567 | BCL6, BTG2, CLEC18C, COL4A3, DENND1B, FMO1, HOXB3, HOXB6, HS35T5, KRT15, KRT23, PDGFRA, PFKFB1, PTPRG, PYY, RNF112, SPRY4, SYT7 |

Enriched TFBS were found using ToppGene server

To further define DEK targets relevant in HNSCC, Applicant performed a walk-based network analysis to assign functional interactions between DEK and its transcriptional targets. A portion of the down-regulated gene network for UMSCC1 cells is shown (FIG. 1D), with arrows highlighting two interconnected nodes. Expanded versions of this network map, along with others, are found in FIG. 1-11. DEK down-regulation was connected to many genes of interest, including TNFAIP3, IL6, and MAPKs. Because these genes are well established for their downstream contributions to inflammation and immune signaling, Applicant focused on the most important upstream transducer of toll-like receptor (TLR) and interleukin-1 receptor (IL-1R) signaling that was repressed following DEK loss, IRAK1.

Interestingly, a recent publication emphasized the importance of IL1R-dependent signaling in HNSCCs. Therein, signaling from the IRAK1 adapter protein MyD88 was increased in response to erlotinib treatment in EGFR-amplified HNSCCs [22]. Furthermore, inhibition of IL1R signaling enhanced sensitivity to erlotinib treatment, thus supporting clinical potential for the targeting of TLR/IL1R signaling pathways in these cancers.

DEK Regulates IRAK1 mRNA and Protein Levels.

Figure 2E:
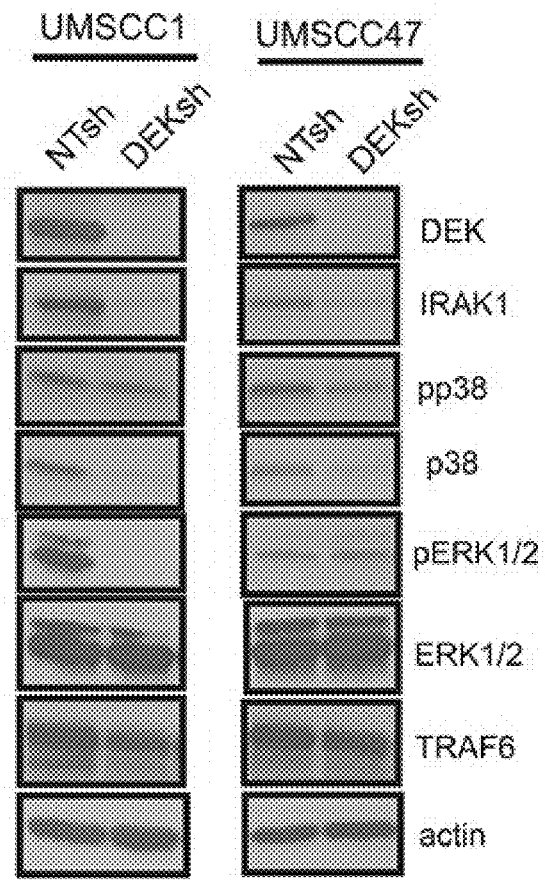

IRAK1 expression was decreased by 1.4- to 3.2-fold upon DEK loss in HNSCC, as determined by RNA-Seq (FIG. 2A). To confirm IRAK1 expression was reduced following DEK depletion, IRAK1 mRNA was independently validated by qRT-PCR in numerous cell lines (FIG. 2B-2D). As expected, IRAK1 mRNA levels were reduced in UMSCC1 and UMSCC47 cell lines, as well as in an additional HPV-HNSCC cell line following DEK knockdown. Similarly, DEK knockdown in these cell lines reduced IRAK1 protein expression levels, along with known MAPK signaling, which are downstream targets of IRAK1 (FIG. 2E). IRAK repression was also observed in two additional DEK-targeted cell lines UMSCC6 (HPV−) and 93VU147T (HPV) (data not shown). Reduced expression of IRAK1 in the absence of DEK was correlated with reduced expression of downstream pathway components, thus suggesting IRAK1 may be a functionally relevant DEK target.

TCGA Data Indicates IRAK1 is Overexpressed in HNSCC.

Figure 3A:
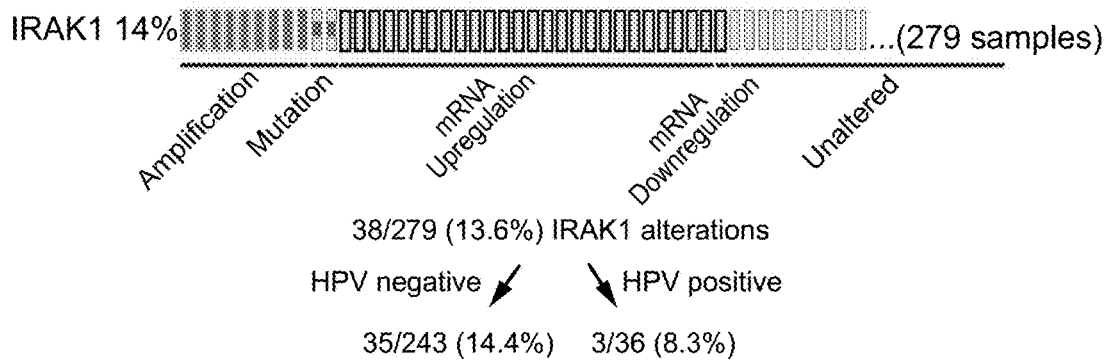
FIG. 3A-3C. TCGA data indicates IRAK1 is overexpressed in HNSCC.
Figure 3B:
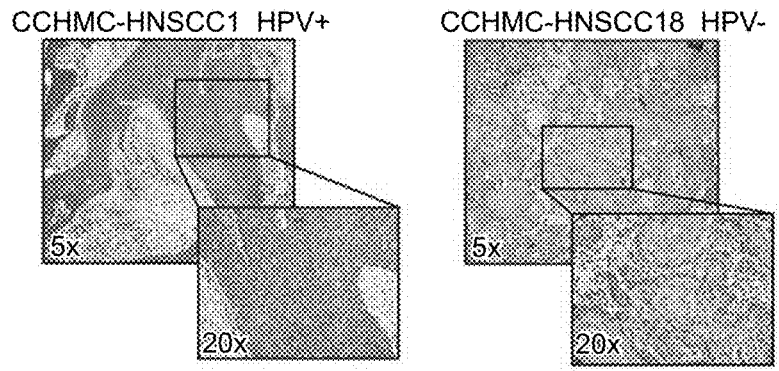
Figure 3C:
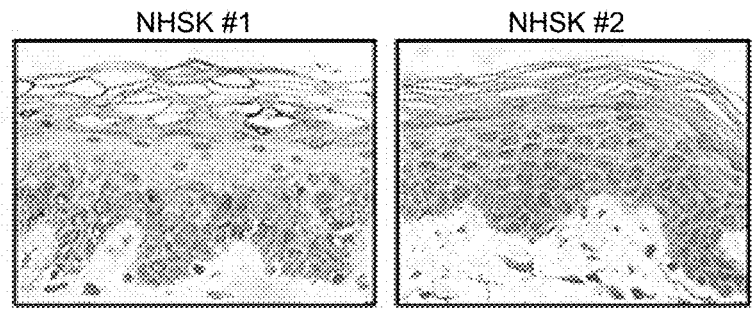

Based on the observed IRAK1 transcriptional regulation in HNSCC cell lines, Applicant evaluated publicly available TOGA databases to determine whether IRAK1 alterations exist in primary HNSCCs. This data mining revealed IRAK1 is altered in 14% of HNSCCs, predominantly as a result of gene amplification or mRNA up-regulation (FIG. 3A). This overexpression was observed in HPV+ and HPV− tumor subsets. To confirm that IRAK1 protein is expressed in HNSCC, Applicant performed immunohistochemistry for IRAK1 on primary HNSCC tissue samples, which were previously described [8].

Examples of HPV+ and HPV− specimens are shown (FIG. 3B), with strong IRAK1 protein expression detectable in the cytoplasm as expected, and some additional nuclear staining. Since adjacent normal tissue was not present in these specimens, Applicant utilized normal human skin from unrelated donors as a control. IRAK1 staining of 3 specimens (n=3) revealed IRAK1 protein expression was absent from well differentiated layers of human epidermis. Together, this data suggests IRAK1 is highly expressed in HNSCC tumors in line with possible oncogenic activities.

IRAK1 Loss Increases Apoptosis in HNSCC.

Figure 4A:
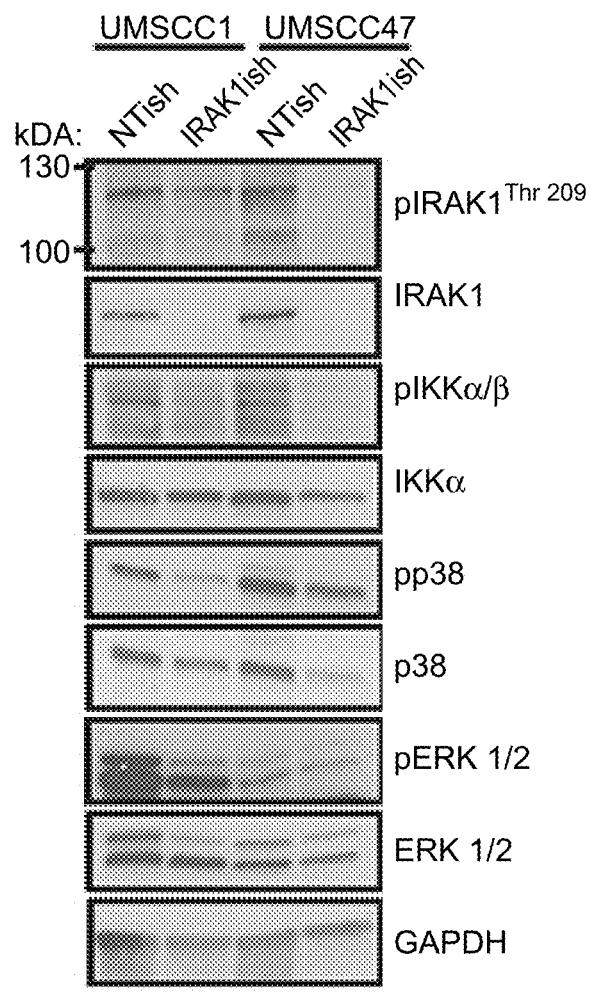
FIG. 4A-FIG. 4G. IRAK1 loss increases apoptosis in HNSCC.
Figure 4B:
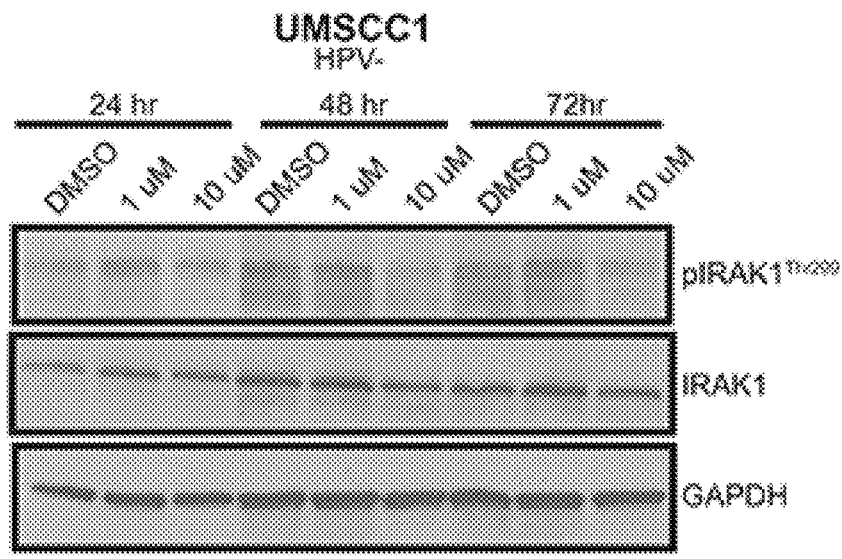
Figure 4C:
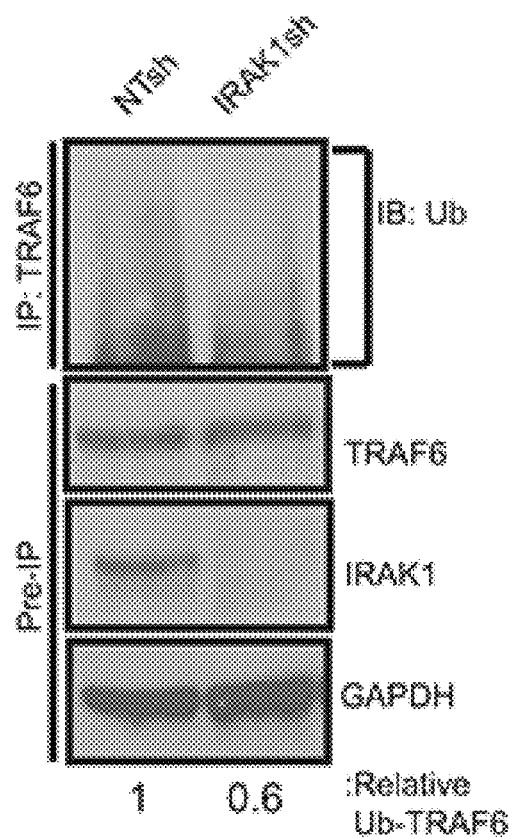
Figure 4D:
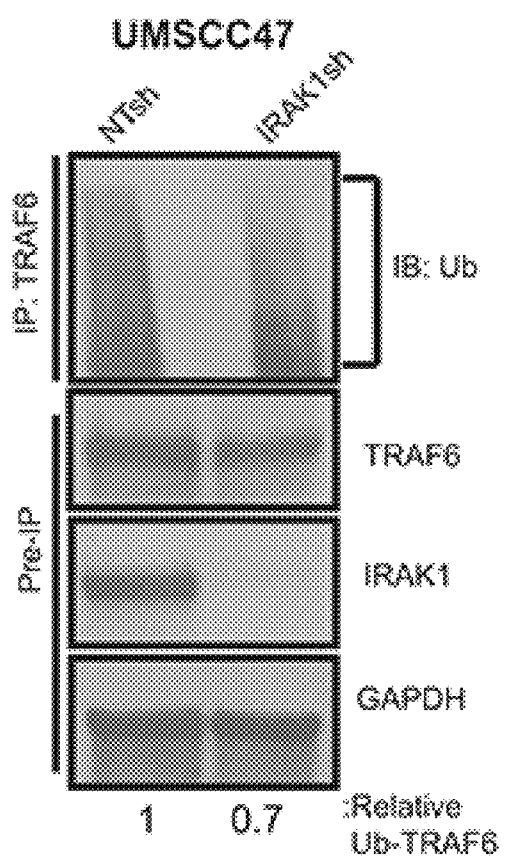

Having identified IRAK1 as a candidate effector in HNSCC Applicant next sought to characterize its function by genetic and pharmacologic inhibition. Previously, IRAK1 was proposed to have a tumor suppressive role in HNSCCs [23]. Therefore, Applicant aimed to determine the contribution of IRAK1 to HNSCC phenotypes. Applicant utilized a published IRAK1 shRNA construct to deplete IRAK1 levels in both HNSCC cell lines [20]. IRAK1 knockdown resulted in decreased total and activated IRAK1, as measured by phosphorylation of residue Thr209. In addition, knockdown of IRAK1 coincided with a reduction in NF-KB (pIKKa/r3) and MAPK (p38 and ERK1/2) signaling (FIG. 4A), both well-known signaling pathways downstream of activated IRAK1. Chemical inhibition of IRAK1 was also carried out with the IRAK-1/4 inhibitor which has been shown to increase apoptosis in melanoma cells in vitro and in vivo and to inhibit signaling and cell viability in MDS [20, 24]. This inhibitor is a benzimidazole that is selective for IRAK1 and IRAK4 and shows little specificity for other kinases [24]. Similar to these published studies, 10 μM concentrations of IRAK-1/4 inhibitor attenuated activation of IRAK1 at 24-72 hours post-treatment (FIG. 4B) in UMSCC1 and UMSCC47 cells. Activated phospho-IRAK1 complexes with TRAF6, which undergoes Lysine(K)-63 conjugated ubiquitination, a measure of its active state, thereby initiating downstream signaling cascades. To verify that signaling effects observed with IRAK1 loss were a result of a reduction in TRAF6-ubiquitination, TRAF6 was immunoprecipitated and subsequently probed for ubiquitin. TRAF6 ubiquitination was decreased in the absence of IRAK1, suggesting that NF-KB and MAPK signaling is mediated through TRAF6 (FIG. 4C-D).

Figure 4E:
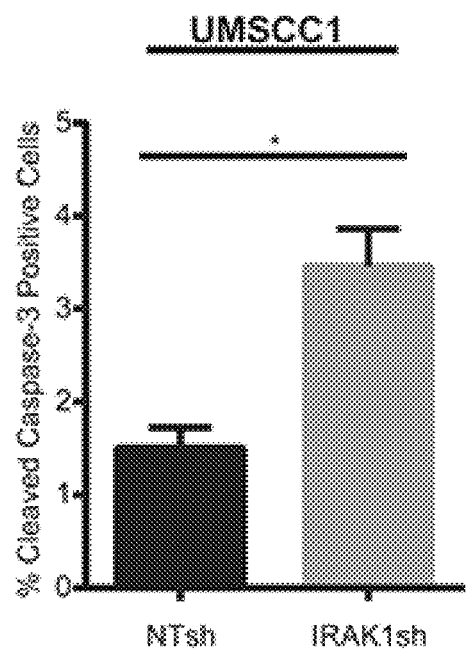
Figure 4F:
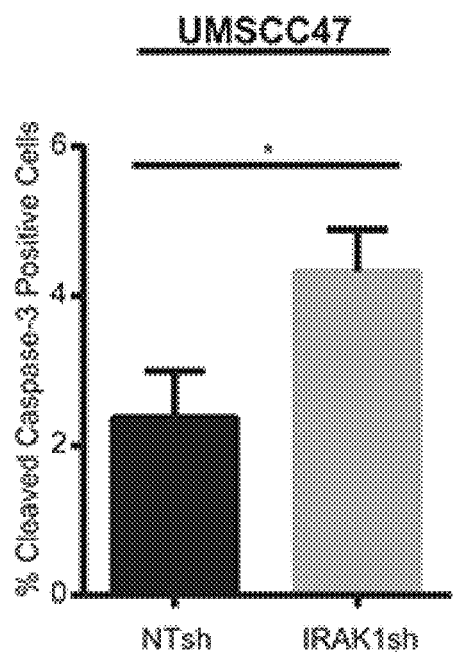
Figure 4G:
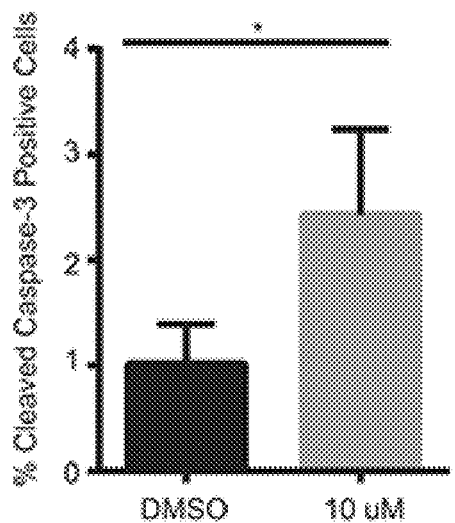

Finally, cellular proliferation and death were assessed upon IRAK1 inhibition to establish a functional role of IRAK1 in HNSCC cells. Significantly increased apoptosis was observed in the absence of IRAK1, either with shRNA or with IRAK1/4-inhibitor (FIG. 4E-4G). However, Applicant did not observe any differences in cell cycle profiles (FIG. 12). These results demonstrate that IRAK1 promotes the survival of HNSCC cells and that IRAK1 inhibition may be a novel therapeutic strategy to enhance cell death in this tumor type.

IRAK1 and DEK Independently Regulate HNSCC Cellular Survival.

Figure 5A:
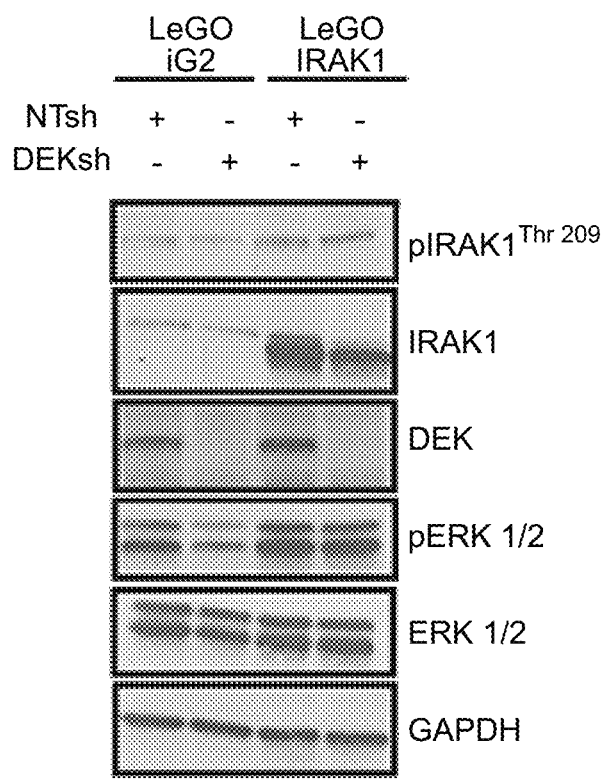
FIG. 5A-FIG. 5F. IRAK1 and DEK depletion cooperate to increase apoptosis.
Figure 5B:
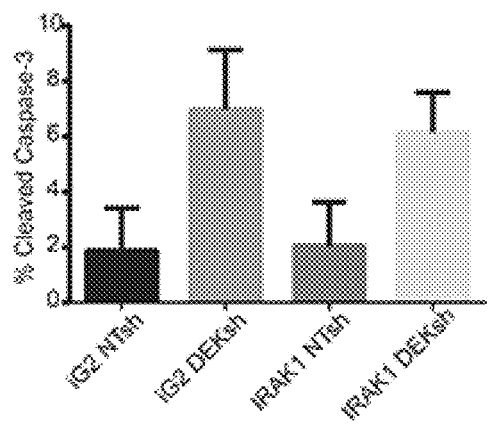
Figure 5C:
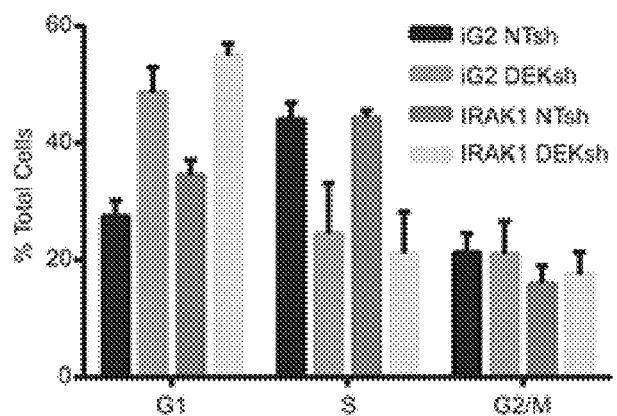
Figure 5D:
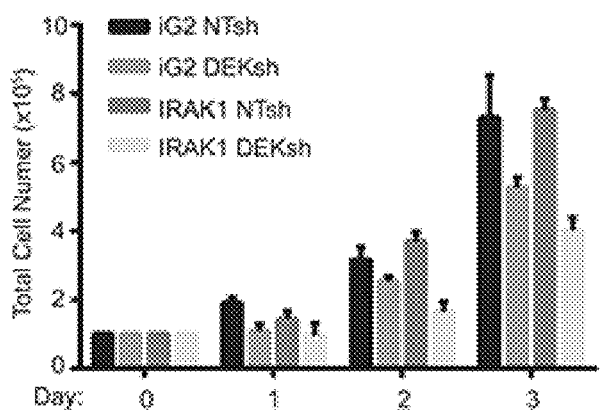
Figure 5E:
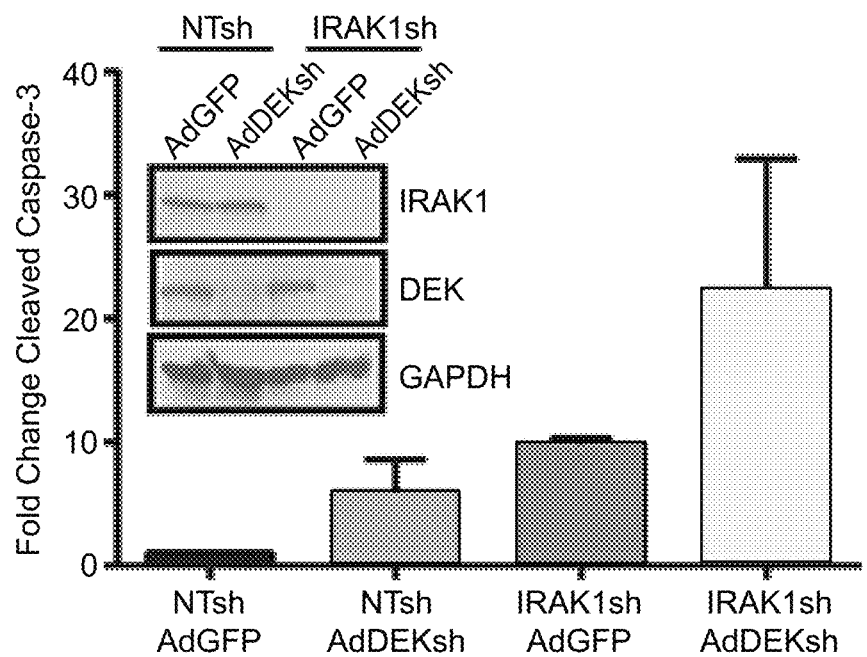
Figure 5F:
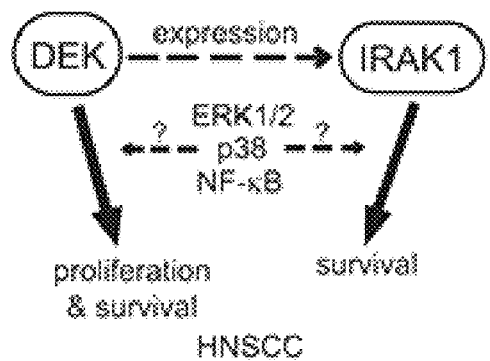
Figure 7:
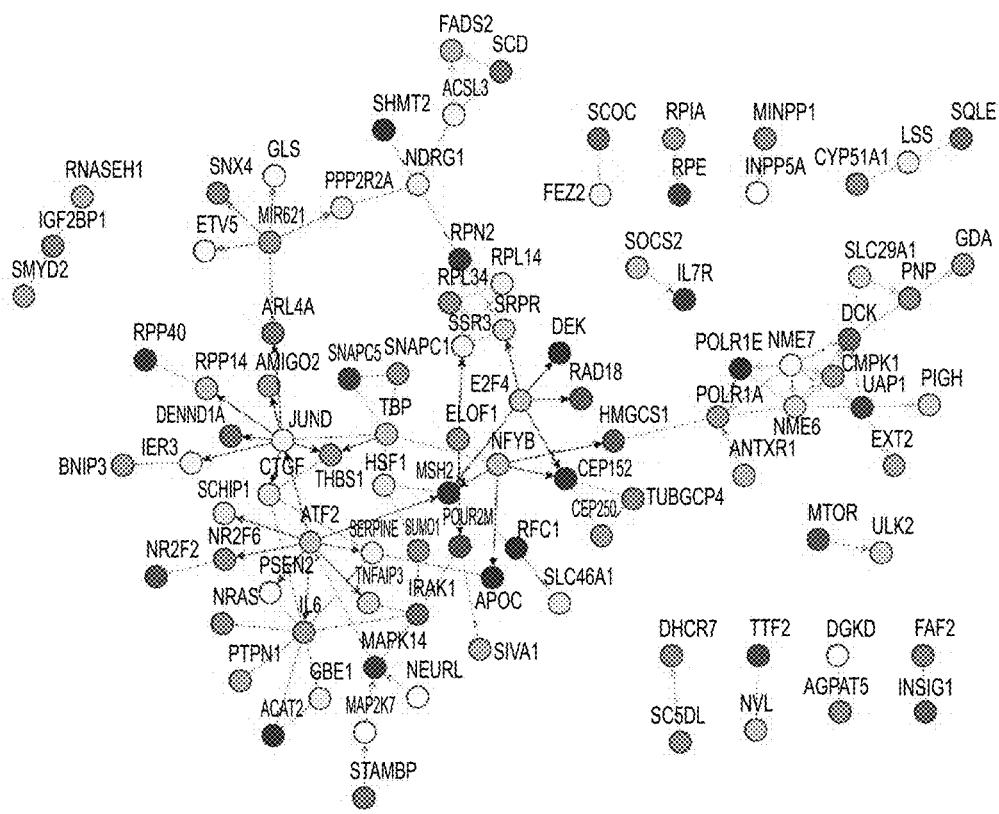
FIG. 7. Network 1 is represented, with genes down-regulated in UMSCC1, with log fold change represented. This is the expanded view of the network map highlighted in FIG. 1.
Figure 8:
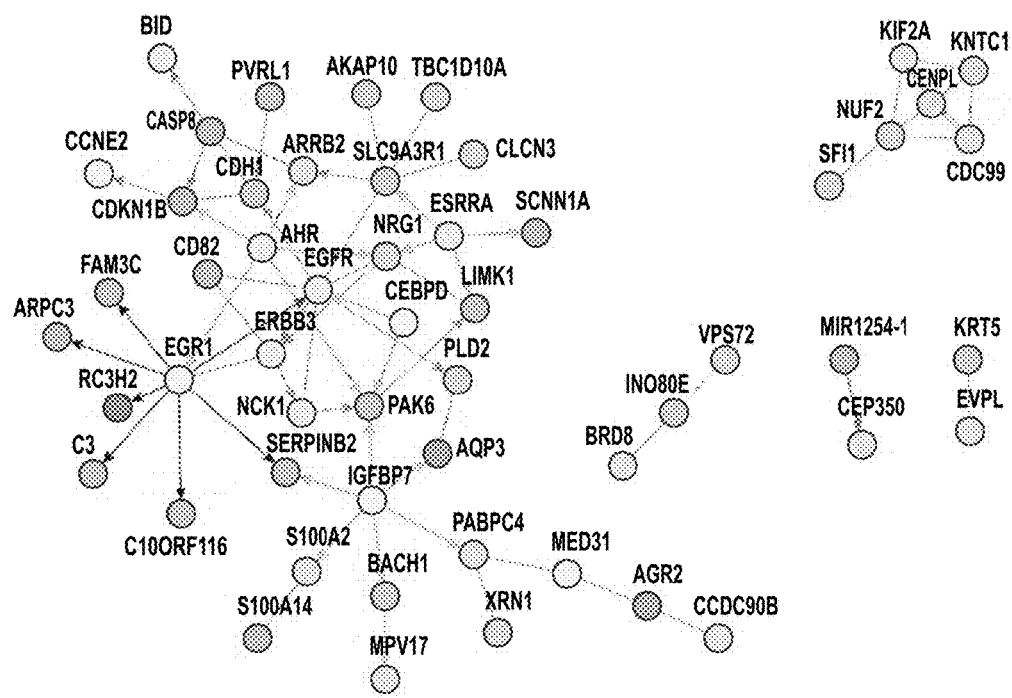
FIG. 8. Network 2 is represented, with genes up-regulated in UMSCC47, with log fold change represented.
Figure 9:
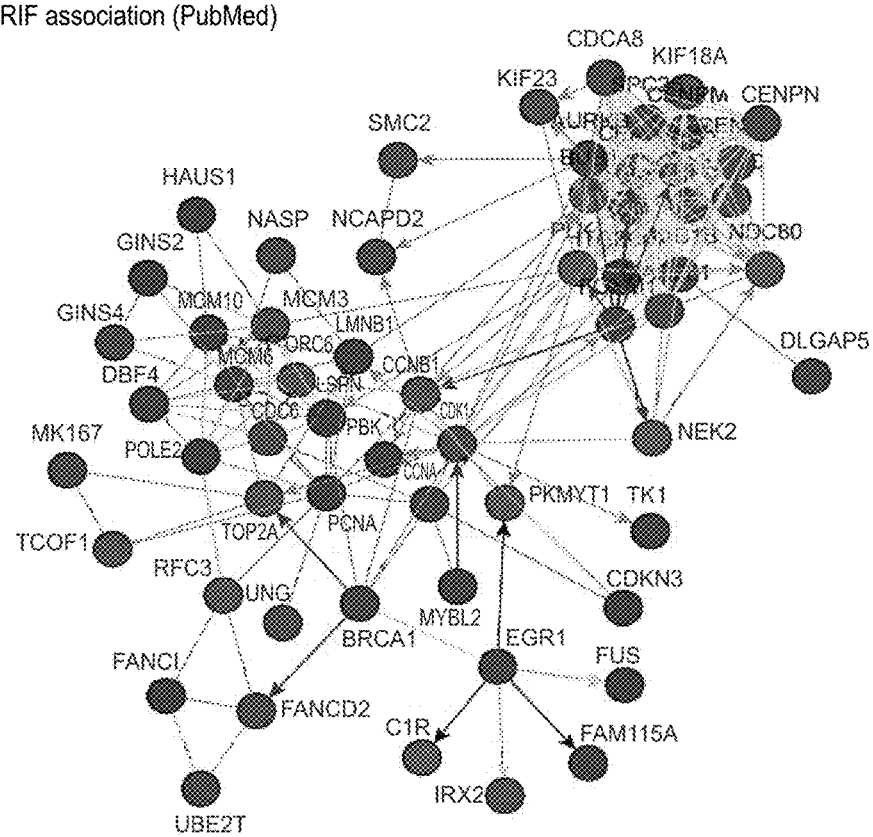
FIG. 9. Network 3 is represented, with genes down-regulated in UMSCC1, with log fold change represented.

To assess if IRAK1 is required for DEK-induced phenotypes in HNSCC, IRAK1 was overexpressed in the presence and absence of DEK (FIG. 5A). Interestingly, IRAK1 overexpression rescued phospho-ERK1/2 signaling (FIG. 5A), but reconstitution of this pathway was not sufficient to rescue cell death (FIG. 5B), cell cycle arrest (FIG. 5C), or total cell number (FIG. 5D) caused by DEK loss. This observation suggests that DEK and IRAK1 independently contribute to HNSCC cell survival. To determine whether DEK and IRAK1 cooperate to regulate the oncogenic phenotype, and therefore, whether targeting DEK and IRAK1 simultaneously will enhance cell death, Applicant used a dual approach of infecting stably transduced IRAK1 knockdown cells with adenovirus to deplete DEK (AdDEKsh). Either DEK or IRAK1 knockdown alone could induce apoptosis as expected (8-10 fold over control), but the combined effect of IRAK1 shRNA with AdDEKsh infection was greater than that of the respective control cells (20-fold) (FIG. 5E). Taken together, these data support a model wherein DEK and IRAK1 function in parallel pathways that control apoptosis, and highlight an additive relationship that may be beneficial for therapeutic intervention (FIG. 5F).

Discussion

A majority of patients with head and neck squamous cell carcinoma present at advanced stages of disease, which contributes to the poor survival outcomes observed. These tumors also notoriously recur, despite aggressive treatment modalities including surgery, chemotherapy and/or radiation therapy, which have frequent side effects that can dramatically and permanently decrease patient quality of life. This suggests these cells have a high proliferative and survival capacity that is necessary for sustained growth of these tumors. Therefore, understanding the relevant targetable mediators of these phenotypes is of the utmost importance. Here Applicant addressed this clinical need by first profiling the transcriptome of HNSCC cell lines that are dependent on the DEK oncogene. DEK is an important regulator of HNSCC growth, and is up-regulated in >90% of primary HNSCCs tested to date [8]. Although some transcriptional DEK targets have been described, the DEK-dependent transcriptome in squamous cell carcinomas remains unknown. Ontology analysis revealed biological processes significantly altered in the absence of DEK, including adhesion, differentiation, immune regulation, and development. This is in contrast to transcriptional data from neuroendocrine carcinoma of the lung with DEK loss. Shibata et al. revealed in their analysis that steroid metabolism, nucleosome assembly, and lipid synthesis and metabolism were altered most often in the absence of DEK [16]. This suggests the effects of DEK loss in malignancies are cell-type dependent.

Here Applicant has identified DEK-dependent gene expression that supports phenotypes previously defined, along with new systems of interest for future studies. Although DEK overexpression is published to promote the migration and invasion of breast and HNSCC cells, alterations in cellular adhesion have not been pursued [25]. Applicant's data suggests this may be one mechanism by which DEK promotes invasion (FIG. 10). Furthermore, Applicant has correlated the DEK-dependent transcriptome with common transcription factor binding sites that are associated with DEK loss (Tables 1-3). Many notable transcription factor binding sites and known targets of DEK were identified, including p53, CEBP, and p65 validating the importance of DEK in multiple cancer types [15, 26]. For example, DEK-dependent control of p53 binding sites was expected given that DEK loss was reported to lead to the stabilization of p53 [21].

This correlated with the up-regulated induction of several p53 regulated genes including BCL11B, KRT15, and PIM1. Applicant focused on the regulation of genes with roles in immune cell signaling. These included NF-KB and MAPK driven genes such as MAPK14, TNFAIP3, IL6, and IRAK1. Applicant chose to probe the role of the IRAK1 serine/threonine kinase, a driver of inflammatory pathways in hematological disease, based on its function as a central signaling hub in the cytoplasm, and as a targetable molecule in MDS and AML.

The role of IRAK1 in solid tumors has not been explored extensively, but Applicant's data suggest oncogenic and potentially targetable activities in HNSCCs. IRAK1 was transcriptionally up-regulated and amplified in a proportion of HNSCCs in the TOGA, in line with a newly discovered functional requirement for maximal survival of HPV positive and negative HNSCC cell lines. Such a role was uncovered through IRAK1 knockdown using stable lentiviral vectors, as well as through chemical inhibition. Downstream IRAK1 signaling was suppressed through TRAF6, attenuating activation of NF-KB and MAPK and stimulating cancer cell death, thus highlighting the potential use of IRAK1 inhibitors in the treatment of HNSCC.

Our data identified IRAK1 as a component of the DEK-dependent transcriptome whose expression in HNSCC contributes to tumor cell survival. IRAK1 drives ERK1/2 signaling, but this alone was not sufficient to rescue cell growth in the absence of DEK. This is not surprising given the large network of genes regulated by DEK and suggests multiple genes are required to maintain a proliferative state. It is also possible that ERK1/2 signaling may be unimportant in, or may modify the response to DEK loss.

Figure 14:
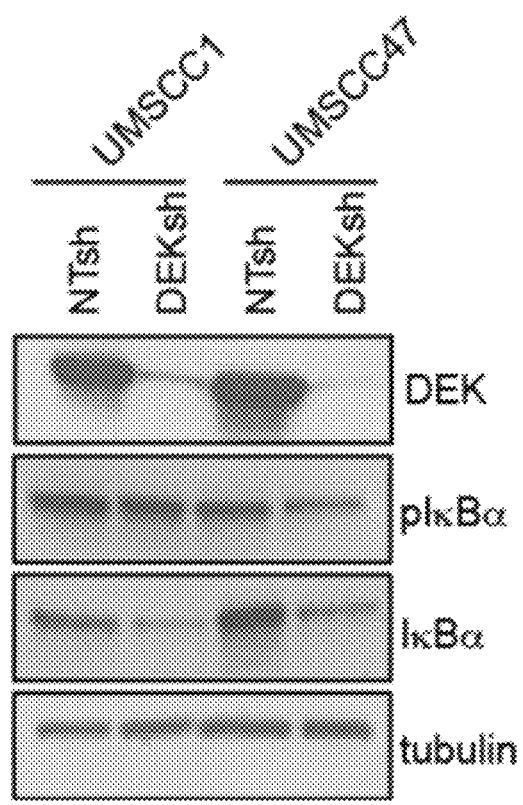
FIG. 14. UMSCC1 and UMSCC47 control (NTsh) and DEK-deficient (DEKsh) lysates were analyzed by western blot for phosphor and total IkBalpha. Tubulin was used as a loading control.

Finally, Applicant investigated a possible effect of DEK loss on NFKB signaling. NFKB can also be activated downstream from the IRAK1 cascade. Western blot data from both cell lines demonstrate an unexpected reduction in total IkBa protein (FIG. 14).

Together, these data suggest DEK/IRAK targeting may in fact activate the NFKB pathway, and highlight unexpected signaling connections between DEK/IRAK1 and NFKB in HNSCC which remain to be defined.

Although IRAK1 was not by itself sufficient to rescue DEK-deficiencies, the combined targeting of DEK and IRAK1 demonstrated an additive relationship. This additive effect emphasizes the large network of signaling hubs through which DEK functions, independent of IRAK1, which can be further extracted from the transcriptional data and explored in future experiments. Importantly, this work has defined IRAK1 as one functionally important driver of HNSCC survival. Interestingly, tumor suppressive functions of IRAK1 have been proposed in a recent publication in oral squamous cell carcinoma cells (OSCC). Hung et al. described miR-146a, a known regulator of IRAK1, as overexpressed in OSCC. Other publications define miR-146a as tumor suppressive, where its loss hyper-activates IRAK1 and may be one mechanism for IRAK1 overexpression [27]. In OSCC, exogenous miR-146a expression increased orthotopic tumors and metastasis of SAS cells and reduced IRAK1 protein levels. In these same cells, IRAK1 knockdown combined with TRAF6 knockdown by siRNA increased invasion and tumor volume, but IRAK1 knockdown alone had few effects [23]. Here, Applicant utilized oropharyngeal HNSCC cells lines wherein IRAK1 surprisingly exhibited oncogenic functions. These opposing findings may be related to the site of origin for each cell line. Additionally, TOGA data wherein IRAK1 is largely over-expressed in HNSCCs supports the hypothesis that IRAK1 contributes to oncogenic phenotypes [23]. Many possibilities exist to explain these discrepancies. IRAK1 functions may be anatomically or cell line dependent, or the method of inhibition may be important (acute (siRNA) versus stable (shRNA)). Additionally, IRAK1 expression may be a double-edged sword and careful balance of its expression might be required. TOGA data in other squamous tumors, such as cervical cancer, identified one patient with homozygous deletion of IRAK1 and two with truncating mutations. The other twenty specimens where IRAK1 was altered were due to copy number amplification and mRNA up-regulation. Overexpression of IRAK would then be a predictive marker of optimal response to IRAK1 inhibitors and may be a fruitful biomarker across various types of malignancies.

Materials & Methods

Cell culture. HPV negative UMSCC1 and UMSCC6, and HPV positive UMSCC47 head and neck cancer cell lines were cultured in DMEM (Gibco, New York, N.Y., USA) supplemented with 1% hydrocortisone (HPV- only), 10% fetal bovine serum, antibiotics and antifungals.

Lentiviral transduction. Cell lines were transduced with lentiviral pLKO.1 vectors for either nontargeting control shRNA (NTsh), IRAK1sh (TRCN0000000543, OpenBiosystems, Lafayette, Colo., USA), or DEK832 (DEKsh, Sigma-Aldrich Mission shRNA library, St Louis, Mo., USA) in the presence of polybrene (8 μg/mL). Cells were selected in puromycin at a final concentration of 1 μg/mL.

Adenoviral transduction. Cells transduced with control (NTsh) and IRAK1 knockdown (IRAK1sh) lentiviruses were plated in equal densities and kept under puromycin selection. 48 hours post-plating cells were transduced with control (AdGFP) or DEK knockdown (AdDEKsh) adenoviral vectors at 10 infectious units per cell as previously published [21]. 72 hours post-transduction, cells and media were collected and fixed to analyze for flow cytometry (see below). IRAK1 and DEK knockdown were confirmed by western blot analysis.

IRAK1 overexpression. UMSCC1 cells were lentivirally transduced with control (LeGo-iG2) or IRAK1 overexpression (LeGO-IRAK1) vectors in the presence of 8 ug/mL polybrene. Cells were sorted based on GFP-positivity and expanded for experiments post-sorting. IRAK1 overexpression did not alter the growth of these cells (FIG. 13). Creation of these vectors has been described previously [28].

cBioPortal Analysis. The results depicted here are in whole or part based upon data generated by the TOGA Research Network: http:hcancergenome.nih.gov [29, 30]. For IRAK1 expression z-score thresholds were set at 2.0.

RNA-Sequencing. Transduced and selected UMSCC1 and UMSCC47 NTsh and DEKsh cells were collected and processed with a ZR RNA MiniPrep kit (R1064, Zymo Research, Irvine, Calif., USA), per kit instructions. A portion of the final RNA isolate for each sample was submitted for quality assurance prior to RNA-Sequencing. RNA-Sequencing was performed by the CCHMC DNA Sequencing and Genotyping Core on an Illumina HiSeq2500 for single-end sequencing with 50 base pair reads. The data discussed in this publication have been deposited in NCBI's Gene Expression Omnibus [31] and are accessible through GEO Series accession number GSE70462 (http://www.ncbi.nlm.nih.gov/geo/query/acc.cgi?acc=GSE70462).

GeneSpring NGS Analysis. RNA-Seq files were imported into GeneSpring Multi-Omic Analysis Software V12.6 (Agilent, Santa Clara, Calif., USA) and sequences were aligned to the reference genome, hg19/GRCh37, which efficiently aligns reads spanning known or novel splice junctions. The reference annotations were produced by the Ensembl project [32]. Aligned reads were filtered on base quality, with a quality threshold >=30. The aligned gene read counts were quantified and used to compute reads per kilobase per million reads (RPKMs) for each transcript in each sample. Raw counts were normalized using the DESeq algorithm and threshold set to 1. Subsequent filtrations removed all genes with fewer than 3 reads in each sample. Fold change was calculated as DEKsh/NTsh with a cut-off of 1.4 fold change. Venn diagrams were created in GeneSpring and entity lists were translated from UMSCC1. Gene lists were submitted to ToppGene (http://toppgene.cchmc.org) for functional enrichment analysis [33].

Network Analysis: All of the network analyses and visualizations were performed using the NetWalker software and were described in detail previously [34].

Transcription factor binding site analysis. In order to identify enriched (p value <0.05) putative transcription factor binding sites within the up- and down-regulated genes, Applicant mined the catalog of human, mouse, rat, and dog conserved regulatory motifs in promoters using the ToppGene server [33, 35].

Quantitative RT-PCR. RNA was collected with Trizol (Invitrogen, Grand Island, N.Y., USA) and reverse transcribed to cDNA using the QuantiTect Reverse Transcription kit (Qiagen, Valencia, Calif., USA). cDNA expression was detected with TaqMan Gene Expression Master Mix and probes (Applied Biosystems). Data was analyzed using the AACt method and values calculated relative to GAPDH. TaqMan probes were as follows: DEK (Hs01078267_m1), IRAK1 (Hs01018347_m1), and GAPDH (Hs02758991_g1).

Western blotting. Whole cell lysates were harvested using Laemmli buffer and a total of 20 µg of protein was analyzed as described previously [21]. Membranes were probed with DEK (1:1000, BD Biosciences, San Jose, Calif., USA), IRAK1 (1:1000, Santa Cruz Biotechnology, Dallas, Tex., USA (sc-7883)), TRAF6 (1:1000, Santa Cruz (sc-7221)), phospho-IRAK1 (Thr209, 1:800, Assay Biotechnology Company (A1074), Sunnyvale, Calif., USA), phospho-p38 (1:500, Cell Signaling Technologies (4361)), p38 (1:1000, Cell Signaling Technologies (9212)), phospho-ERK1/2 (1:1000, Cell Signaling Technologies (4377)), ERK1/2 (1:1000, Cell Signaling Technologies (4695)), phospho-IKKa/r3 (1:500, Cell Signaling Technologies (2697)), IKKa (1:1000, Cell Signaling Technologies (2682)), phospho-hcBa (1:500, Cell Signaling Technologies (9246)), hcBa (1:1000, Cell Signaling Technologies (4812)), a-tubulin-HRP (1:10,000 Cell Signaling Technologies (9099)), actin (1:10,000 a gift from James Lessard), and GAPDH (1:1000, Cell Signaling Technologies (5174)).

Flow cytometry for Cleaved Caspase-3. Lentivirally transduced cells were plated at equal densities and collected 48 hours later. Cells were fixed and prepped following the BD FITC Active Caspase-3 Apoptosis kit protocol (BD Biosciences). Adenovirally transduced cells were prepped with an Alexa-Fluor 647 conjugated cleaved-caspase 3 antibody to account for GFP-positivity (Cell Signaling Technologies (9602)). Analysis was performed on a BD FacsCanto and data analyzed on FlowJo software (Tree Star, Ashland, Oreg., USA). Experiments were performed 3 times with standard error of the mean (SEM) represented.

Flow cytometry for cell cycle analysis. Lentivirally transduced cells were plated in equal numbers and 48 hours later were pulsed with 10 µM BrdU for 45 minutes. Cells were collected and prepped following the BD Pharmigen APC BrdU flow kit and analyzed on a BD FacsCanto. Data was analyzed on FlowJo Software as above. Experiments were performed 3 times and SEM represented.

IRAK1 inhibitor. UMSCC1 cells were plated at equal densities and IRAK1 inhibitor (IRAK-1/4 inhibitor, 15409, Sigma-Aldrich, St. Louis, Mo., USA) added the same day for caspase-3 flow cytometry experiments. DMSO was added in equal volume for a control.

Cells and media were collected 72 hours later and prepared and analyzed as above. For the time-course experiment, cells were plated and inhibitor was added the following day, with protein collected at 24, 48, and 72 hours and analyzed by western blot for IRAK1 inhibition.

Immunohistochemistry. The IRB-approved collection of primary human tumor tissue specimens and immunohistochemistry staining protocol were previously described [8]. Sections from n=4 primary tumor specimens and n=3 normal human skin samples were probed with IRAK1 antibody (1:50, se-7883, Santa Cruz). Skin samples were obtained from consented donors at Cincinnati Children's Hospital Medical Center in accordance with an approved IRB protocol. Images were captured with a Leica DM2500 microscope and LAS software (Leica Microsystems Inc., Buffalo Grove, Ill., USA) at the indicated magnifications.

TRAF6 Immunoprecipitation. Samples were lysed using RIPA buffer containing protease and phosphatase inhibitors and protein concentration determined using BCA Protein Assay Kit (Pierce 23225). 600 µg of each sample was used to perform TRAF6 immunoprecipitation. Lysates were incubated with A/G beads (sc-2003, Santa Cruz, Dallas, Tex., USA) and incubated with TRAF6 antibody (se-7221, Santa Cruz). Samples were loaded onto a 4-15% gradient Mini-PROTEAN TGX Precast Gel (BioRad, Hercules, Calif., USA) and proteins separated by SDS-PAGE electrophoresis. Membranes were probed with ubiquitin primary antibody (se-8017, Santa Cruz). Protein from the original lysis, prior to immunoprecipitation, was run following the above western blot protocol. Membranes were probed with IRAK1, TRAF6, and GAPDH. Densitometry was performed using ImageJ software.

Growth Curves. Control and IRAK1 overexpressing cells were plated at equal densities, in triplicate, and total cell number counted over 3 days. Experiments were performed twice with SD represented.

Statistics. Statistical analysis was performed using Graph-Pad Prism 6 software (La Jolla, Calif., USA). Student's t-test was used to calculate p-values, where *=p.05 and **=p.01.

REFERENCES

1. Chaturvedi A K, Engels E A, Pfeiffer R M, Hernandez B Y, Xiao W, Kim E, Jiang B, 556 Goodman M T, Sibug-Saber M, Cozen W, Liu L, Lynch C F, Wentzensen N, Jordan R C, Altekruse S, Anderson W F, et al. Human papillomavirus and rising oropharyngeal cancer incidence in the United States. J Clin Oncol. 2011; 29(32):4294-4301.

2. Ang K K, Harris J, Wheeler R, Weber R, Rosenthal D I, Nguyen-Tan P F, Westra W H, Chung C H, Jordan R C, Lu C, Kim H, Axelrod R, Silverman C C, Redmond K P and Gillison M L. Human papillomavirus and survival of patients with oropharyngeal cancer. N Engl J Med. 2010; 363(1):24-35.

3. Marur S and Forastiere A A. Head and neck cancer: changing epidemiology, diagnosis, and treatment. Mayo Clinic proceedings. 2008; 83(4):489-501.

4. Privette Vinnedge L M, Ho S M, Wikenheiser-Brokamp K A and Wells S I. The DEK oncogene is a target of steroid hormone receptor signaling in breast cancer. PloS one. 2012; 7(10): e46985.
5. Privette Vinnedge L M, McClaine R, Wagh P K, Wikenheiser-Brokamp K A, Waltz S E and Wells S I. The human DEK oncogene stimulates beta-catenin signaling, invasion and mammosphere formation in breast cancer. Oncogene. 30(24):2741-2752.
6. Khodadoust M S, Verhaegen M, Kappes F, Riveiro-Falkenbach E, Cigudosa J C, Kim D S, Chinnaiyan A M, Markovitz D M and Soengas M S. Melanoma proliferation and chemoresistance controlled by the DEK oncogene. Cancer Res. 2009; 69(16):6405-6413.
7. Datta A, Adelson M E, Mogilevkin Y, Mordechai E, Sidi A A and Trama J P. Oncoprotein DEK as a tissue and urinary biomarker for bladder cancer. BMC cancer. 2011; 11:234.
8. Adams A K, Hallenbeck G E, Casper K A, Patil Y J, Wilson K M, Kimple R J, Lambert P F, Witte D P, Xiao W, Gillison M L, Wikenheiser-Brokamp K A, Wise-Draper T M and Wells S I. DEK promotes HPV-positive and -negative head and neck cancer cell proliferation. Oncogene. 2014; 0:1.
9. Alexiadis V, Waldmann T, Andersen J, Mann M, Knippers R and Gruss C. The protein encoded by the proto-oncogene DEK changes the topology of chromatin and reduces the efficiency of DNA replication in a chromatin-specific manner. Genes Dev. 2000; 14(11):1308-1312.
10. Sawatsubashi S, Murata T, Lim J, Fujiki R, Ito S, Suzuki E, Tanabe M, Zhao Y, Kimura S, Fujiyama S, Ueda T, Umetsu D, Ito T, Takeyama K and Kato S. A histone chaperone, DEK, transcriptionally coactivates a nuclear receptor. Genes Dev. 2010; 24(2):159-170.
11. Kavanaugh G M, Wise-Draper T M, Morreale R J, Morrison M A, Gole B, Schwemberger S, Tichy E D, Lu L, Babcock G F, Wells J M, Drissi R, Bissler J J, Stambrook P J, Andreassen P R, Wiesmuller L and Wells S I. The human DEK oncogene regulates DNA damage response signaling and repair. Nucleic Acids Res.
12. Sanden C, Jarvstrat L, Lennartsson A, Brattas P L, Nilsson B and Gullberg U. The DEK oncoprotein binds to highly and ubiquitously expressed genes with a dual role in their transcriptional regulation. Molecular cancer. 2014; 13:215.
13. Ko S I, Lee I S, Kim J Y, Kim S M, Kim D W, Lee K S, Woo K M, Baek J H, Choo J K and Seo S B. Regulation of histone acetyltransferase activity of p300 and PCAF by proto-oncogene protein DEK. FEBS letters. 2006; 580 (13):3217-3222.
14. Campillos M, Garcia M A, Valdivieso F and Vazquez J. Transcriptional activation by AP-2alpha is modulated by the oncogene DEK. Nucleic Acids Res. 2003; 31(5):1571-1575.
15. Sammons M, Wan S S, Vogel N L, Mientjes E J, Grosveld G and Ashburner B P. Negative regulation of the RelA/p65 transactivation function by the product of the DEK proto-oncogene. J Biol Chem. 2006; 281(37): 26802-26812.
16. Shibata T, Kokubu A, Miyamoto M, Hosoda F, Gotoh M, Tsuta K, Asamura H, Matsuno Y, Kondo T, Imoto I, Inazawa J and Hirohashi S. DEK oncoprotein regulates transcriptional modifiers and sustains tumor initiation activity in high-grade neuroendocrine carcinoma of the lung. Oncogene. 2010; 29(33):4671-4681.
17. Mor-Vaknin N, Punturieri A, Sitwala K, Faulkner N, Legendre M, Khodadoust M S, Kappes F, Ruth R I, Koch A, Glass D, Petruzzelli L, Adams B S and Markovitz D M. The DEK nuclear autoantigen is a secreted chemotactic factor. Mol Cell Biol. 2006; 26(24):9484-9496.
18. Mor-Vaknin N, Kappes F, Dick A E, Legendre M, Damoc C, Teitz-Tennenbaum S, Kwok R, Ferrando-May E, Adams B S and Markovitz D M. DEK in the synovium of patients with juvenile idiopathic arthritis: characterization of DEK antibodies and posttranslational modification of the DEK autoantigen. Arthritis and rheumatism. 2011; 63(2):556-567.
19. Rhyasen G W and Starczynowski D T. IRAK signalling in cancer. British journal of cancer. 2014.
20. Rhyasen G W, Bolanos L, Fang J, Jerez A, Wunderlich M, Rigolino C, Mathews L, Ferrer M, Southall N, Guha R, Keller J, Thomas C, Beverly L J, Cortelezzi A, Oliva E N, Cuzzola M, et al. Targeting IRAK1 as a therapeutic approach for myelodysplastic syndrome. Cancer Cell. 2013; 24(1):90-104.
21. Wise-Draper T M, Allen H V, Jones E E, Habash K B, Matsuo H and Wells S I. Apoptosis inhibition by the human DEK oncoprotein involves interference with p53 functions. Mol Cell Biol. 2006; 26(20):7506-7519.
22. Koch A T, Love-Homan L, Espinosa-Cotton M, Stanam A and Simons A L. MyD88-Dependent Signaling Decreases the Antitumor Efficacy of Epidermal Growth Factor Receptor Inhibition in Head and Neck Cancer Cells. Cancer Res. 2015; 75(8):1657-1667.
23. Hung P S, Liu C J, Chou C S, Kao S Y, Yang C C, Chang K W, Chiu T H and Lin S C. miR-146a enhances the oncogenicity of oral carcinoma by concomitant targeting of the TRAM, TRAF6 and NUMB genes. PloS one. 2013; 8(11): e79926.
24. Srivastava R, Geng D, Liu Y, Zheng L, Li Z, Joseph M A, McKenna C, Bansal N, Ochoa A and Davila E. Augmentation of therapeutic responses in melanoma by inhibition of IRAK-1,-4. Cancer Res. 2012; 72(23):6209-6216.
25. Privette Vinnedge L M, Benight N M, Wagh P K, Pease N A, Nashu M A, Serrano-Lopez J, Adams A K, Cancelas J A, Waltz S E and Wells S I. The DEK oncogene promotes cellular proliferation through paracrine Wnt signaling in Ron receptor-positive breast cancers. Oncogene. 2014.
26. Koleva R I, Ficarro S B, Radomska H S, Carrasco-Alfonso M J, Alberta J A, Webber 643 JT, Luckey C J, Marcucci G, Tenen D G and Marto J A. C/EBPalpha and DEK 644 coordinately regulate myeloid differentiation. Blood. 2012; 119(21):4878-4888.
27. Starczynowski D T, Kuchenbauer F, Argiropoulos B, Sung S, Morin R, Muranyi A, Hirst M, Hogge D, Marra M, Wells R A, Buckstein R, Lam W, Humphries R K and Karsan A. Identification of miR-145 and miR-146a as mediators of the 5q-syndrome phenotype. Nat Med. 2010; 16(1):49-58.
28. Fang J, Rhyasen G, Bolanos L, Rasch C, Varney M, Wunderlich M, Goyama S, Jansen G, Cloos J, Rigolino C, Cortelezzi A, Mulloy J C, Oliva E N, Cuzzola M and Starczynowski D T. Cytotoxic effects of bortezomib in myelodysplastic syndrome/acute myeloid leukemia depend on autophagy-mediated lysosomal degradation of TRAF6 and repression of PSMA1. Blood. 2012; 120(4): 858-867.
29. Gao J, Aksoy B A, Dogrusoz U, Dresdner G, Gross B, Sumer S O, Sun Y, Jacobsen A, Sinha R, Larsson E, Cerami E, Sander C and Schultz N. Integrative analysis of complex cancer genomics and clinical profiles using the cBioPortal. Science signaling. 2013; 6(269): p 11.

30. Cerami E, Gao J, Dogrusoz U, Gross B E, Sumer S O, Aksoy B A, Jacobsen A, 659 Byrne C J, Heuer M L, Larsson E, Antipin Y, Reva B, Goldberg A P, Sander C and Schultz N. The cBio cancer genomics portal: an open platform for exploring multidimensional cancer genomics data. Cancer discovery. 2012; 2(5):401-404.
31. Edgar R, Domrachev M and Lash A E. Gene Expression Omnibus: NCBI gene expression and hybridization array data repository. Nucleic Acids Res. 2002; 30(1):207-210.
32. Flicek P, Amode M R, Barrell D, Beal K, Brent S, Carvalho-Silva D, Clapham P, Coates G, Fairley S, Fitzgerald S, Gil L, Gordon L, Hendrix M, Hourlier T, Johnson N, Kahari A K, et al. Ensembl 2012. Nucleic Acids Res. 2012; 40 (Database issue): D84-90.
33. Chen J, Bardes E E, Aronow B J and Jegga A G. ToppGene Suite for gene list enrichment analysis and candidate gene prioritization. Nucleic Acids Res. 2009; 37 (Web Server issue): W305-311.
34. Komurov K, Dursun S, Erdin S and Ram P T. NetWalker: a contextual network analysis tool for functional genomics. BMC genomics. 2012; 13:282.
35. Xie X, Lu J, Kulbokas E J, Golub T R, Mootha V, Lindblad-Toh K, Lander E S and Kellis M. Systematic discovery of regulatory motifs in human promoters and 3' UTRs by comparison of several mammals. Nature. 2005; 434(7031):338-345.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method of treating head and/or neck squamous cell carcinoma in an individual, comprising the step of administering to said individual a composition comprising an interleukin-1 receptor-associated kinase 1 (IRAK1) inhibitor, wherein said head and/or neck squamous cell carcinoma is characterized by IRAK1 overexpression in a cell or tissue of said head and/or neck squamous cell carcinoma.

2. The method of claim 1, wherein said head and/or neck squamous cell carcinoma is characterized by DEK overexpression.

3. The method of claim 1, wherein said head and/or neck squamous cell carcinoma is human papillomavirus (PV) positive.

4. The method of claim 1, wherein said head and/or neck squamous cell carcinoma is human papillomavirus (PV) negative.

5. The method of claim 1 wherein said IRAK1 and/or an IRAK1/4 inhibitor is selected from N-acyl-2-aminobenzimidazoles, imidazo[1,2-a]pyridino-pyrimidine, imidazo[1,2-a]pyridino-pyridine, benzimidazolo-pyridine, N-(2-morpholinylethyl)-2-(3-nitrobenzoylamido)-benzimidazole,

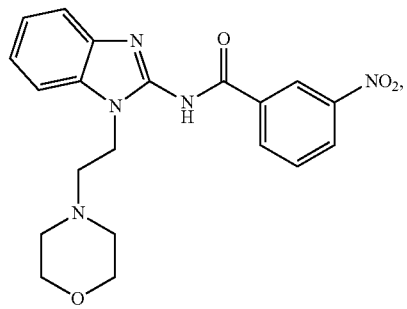 [SMILES: O=C(Nc1nc2ccccc2n1CCN1CCOCC1)c1cccc([N+](=O)[O-])c1]

LG0250276, or combinations thereof.

6. The method of claim 1 wherein said IRAK1 and/or an IRAK1/4 inhibitor comprises an RNAi sufficient to inhibit IRAK1 expression.

7. The method of claim 1, wherein said administering step is selected from orally, rectally, nasally, topically, parenterally, subcutaneously, intramuscularly, intravenously, transdermally, or a combination thereof.

8. The method of claim 1, wherein said administration decreases the growth or metastasis of said head and/or neck squamous cell carcinoma in said individual, as compared to an individual not receiving said composition.

9. The method of claim 1, wherein said method decreases a marker of viability of head and/or neck squamous cell carcinoma cells.

10. The method of claim 1, wherein said treatment decreases a marker of viability of head and/or neck squamous cell carcinoma, wherein marker is selected from survival over time, proliferation, growth, migration, formation of colonies, chromatic assembly, DNA binding, RNA metabolism, cell migration, cell adhesion, inflammation, or a combination thereof.

11. The method according to claim 1, wherein the composition further comprises an inhibitor of DEK.

* * * * *

UNITED STATES PATENT AND TRADEMARK OFFICE
CERTIFICATE OF CORRECTION

PATENT NO. : 10,487,329 B2
APPLICATION NO. : 15/765824
DATED : November 26, 2019
INVENTOR(S) : Wells et al.

Page 1 of 1

It is certified that error appears in the above-identified patent and that said Letters Patent is hereby corrected as shown below:

In the Claims

Column 32, the line before Claim 6, delete "LG0250276,".

Signed and Sealed this
Twenty-sixth Day of May, 2020

Andrei Iancu
*Director of the United States Patent and Trademark Office*